US012782361B2

(12) United States Patent
Murray et al.

(10) Patent No.: US 12,782,361 B2
(45) Date of Patent: Nov. 3, 2026

(54) IDENTIFICATION AND MONITORING OF ACID HYDROLYSIS PRODUCTS OF IMMUNOGLOBULIN HEAVY CHAINS

(71) Applicant: Mayo Foundation for Medical Education and Research, Rochester, MN (US)

(72) Inventors: David L. Murray, Rochester, MN (US); David R. Barnidge, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 928 days.

(21) Appl. No.: 16/646,296

(22) PCT Filed: Sep. 13, 2018

(86) PCT No.: PCT/US2018/050846
§ 371 (c)(1),
(2) Date: Mar. 11, 2020

(87) PCT Pub. No.: WO2019/055631
PCT Pub. Date: Mar. 21, 2019

(65) Prior Publication Data

US 2020/0271663 A1 Aug. 27, 2020

Related U.S. Application Data

(60) Provisional application No. 62/558,056, filed on Sep. 13, 2017.

(51) Int. Cl.
*G01N 33/68* (2006.01)

(52) U.S. Cl.
CPC ..... *G01N 33/6848* (2013.01); *G01N 33/6857* (2013.01); *G01N 33/6893* (2013.01)

(58) Field of Classification Search
None
See application file for complete search history.

(56) References Cited

U.S. PATENT DOCUMENTS 8,501,907 B2 8/2013 Jordan et al.
8,679,767 B2 3/2014 Kaur et al.
(Continued)

FOREIGN PATENT DOCUMENTS

CA 2607197 11/2006
CN 103497254 1/2014
(Continued)

OTHER PUBLICATIONS

Wang et al. "Structural comparison of two anti-CD20 monoclonal antibody drug products using middle-down mass spectrometry." Analyst. May 21, 2013; 138(10):3058-65 (Year: 2013).*
(Continued)

*Primary Examiner* — Rebecca M Giere
*Assistant Examiner* — Alexander Alexandrovic Volkov
(74) *Attorney, Agent, or Firm* — Fish & Richardson P.C.

(57) ABSTRACT

This document provides materials and methods for identifying and/or quantifying immunoglobulin heavy chains (e.g., IgG heavy chains) in a sample, such as a biological sample, using mass spectrometry techniques. For example, mass spectrometry techniques that can be used to identify and/or quantify IgG heavy chain acid hydrolysis products in a serum sample without the need for any IgG cleavage reagents (e.g., enzymes) are provided.

16 Claims, 6 Drawing Sheets

Specification includes a Sequence Listing.

(56) References Cited

U.S. PATENT DOCUMENTS

| | | | |
|---|---|---|---|
| 2002/0182649 | A1 | 12/2002 | Weinberger et al. |
| 2003/0027216 | A1 | 2/2003 | Kiernan et al. |
| 2005/0009009 | A1 | 1/2005 | Peiris et al. |
| 2005/0064422 | A1 | 3/2005 | Barnidge et al. |
| 2005/0191677 | A1 | 9/2005 | Franzen et al. |
| 2005/0232929 | A1 | 10/2005 | Kadkhodayan et al. |
| 2006/0024296 | A1 | 2/2006 | Williams |
| 2006/0281122 | A1 | 12/2006 | Bryant |
| 2007/0015222 | A1 | 1/2007 | Kaneko et al. |
| 2007/0041979 | A1 | 2/2007 | Raju et al. |
| 2007/0054407 | A1 | 3/2007 | Chen et al. |
| 2007/0105181 | A1 | 5/2007 | Pope et al. |
| 2007/0184470 | A1 | 8/2007 | Arman et al. |
| 2007/0259398 | A1 | 11/2007 | Arnott et al. |
| 2007/0292441 | A1 | 12/2007 | Glover et al. |
| 2008/0026949 | A1 | 1/2008 | Hoidal et al. |
| 2008/0064055 | A1 | 3/2008 | Bryant |
| 2008/0131882 | A1 | 6/2008 | Rasmussen et al. |
| 2008/0142696 | A1 | 6/2008 | Geromanos et al. |
| 2008/0166742 | A1 | 7/2008 | Bradwell |
| 2008/0171312 | A1 | 7/2008 | Ley et al. |
| 2008/0317745 | A1 | 12/2008 | Boruchov et al. |
| 2009/0155280 | A1 | 6/2009 | Jordan et al. |
| 2009/0186423 | A1 | 7/2009 | Frandsen |
| 2009/0203602 | A1 | 8/2009 | Gelber et al. |
| 2009/0258828 | A1 | 10/2009 | Beuerman et al. |
| 2010/0015652 | A1 | 1/2010 | Granda et al. |
| 2010/0086922 | A1 | 4/2010 | Bryant |
| 2010/0167267 | A1 | 7/2010 | Schulzknappe et al. |
| 2010/0190652 | A1 | 7/2010 | Nagalla et al. |
| 2010/0261216 | A1 | 10/2010 | Eser et al. |
| 2010/0323381 | A1 | 12/2010 | Bergen, III et al. |
| 2011/0065199 | A1 | 3/2011 | Kuge et al. |
| 2011/0117021 | A1 | 5/2011 | Smith et al. |
| 2011/0151494 | A1 | 6/2011 | Koomen et al. |
| 2011/0183426 | A1 | 7/2011 | Chan et al. |
| 2011/0294150 | A1 | 12/2011 | Koll et al. |
| 2012/0014940 | A1 | 1/2012 | Preuss et al. |
| 2012/0208295 | A1 | 8/2012 | Wang et al. |
| 2012/0309040 | A1 | 12/2012 | Madian et al. |
| 2012/0315645 | A1 | 12/2012 | Kaur et al. |
| 2012/0322073 | A1 | 12/2012 | Lopez-Girona |
| 2013/0040851 | A1 | 2/2013 | Hanzawa et al. |
| 2013/0149389 | A1 | 6/2013 | Flora et al. |
| 2013/0178370 | A1 | 7/2013 | Lavnder et al. |
| 2013/0178385 | A1 | 7/2013 | Bahn et al. |
| 2013/0185096 | A1 | 7/2013 | Giusti |
| 2013/0260406 | A1 | 10/2013 | Koomen et al. |
| 2013/0302821 | A1 | 11/2013 | Sakamoto et al. |
| 2014/0045276 | A1 | 2/2014 | Singh et al. |
| 2014/0186332 | A1 | 7/2014 | Ezrn et al. |
| 2014/0242072 | A1 | 8/2014 | Hansson |
| 2014/0242624 | A1 | 8/2014 | Valliere-Douglass |
| 2014/0249049 | A1 | 9/2014 | Stoll et al. |
| 2014/0308277 | A1 | 10/2014 | Gennaro et al. |
| 2015/0051839 | A1 | 2/2015 | Harding et al. |
| 2015/0204884 | A1 | 7/2015 | Robblee |
| 2015/0219665 | A1 | 8/2015 | Chapple et al. |
| 2015/0276771 | A1 | 10/2015 | Madasamy |
| 2015/0340219 | A1 | 11/2015 | Mellors |
| 2015/0362506 | A1 | 12/2015 | Zhu et al. |
| 2016/0033511 | A1 | 2/2016 | Pannell et al. |
| 2016/0041184 | A1 | 2/2016 | Barnidge et al. |
| 2016/0047819 | A1 | 2/2016 | Viscom et al. |
| 2016/0206660 | A1 | 7/2016 | Shi et al. |
| 2016/0231329 | A1 | 8/2016 | Olsson et al. |
| 2016/0257763 | A1 | 9/2016 | Von Kreudenstein et al. |
| 2016/0349269 | A1 | 12/2016 | Hunt et al. |
| 2017/0023584 | A1 | 1/2017 | Murray et al. |
| 2017/0044608 | A1 | 2/2017 | Wang et al. |
| 2017/0205423 | A1 | 7/2017 | Higel et al. |
| 2017/0336419 | A1 | 11/2017 | Tran et al. |
| 2018/0106815 | A1 | 4/2018 | Barnidge et al. |
| 2018/0267057 | A1 | 9/2018 | Barnidge et al. |
| 2019/0195888 | A1 | 6/2019 | Barnidge et al. |
| 2020/0003784 | A1 | 1/2020 | Murray et al. |
| 2020/0284800 | A1 | 9/2020 | Murray et al. |
| 2020/0292556 | A1 | 9/2020 | Murray et al. |
| 2020/0341003 | A1 | 10/2020 | Murray et al. |

FOREIGN PATENT DOCUMENTS

| | | |
|---|---|---|
| EP | 1329719 | 7/2003 |
| EP | 3270154 | 1/2018 |
| JP | 2009-114092 | 5/2009 |
| SG | 183701 | 9/2012 |
| WO | WO 2003/050517 | 6/2003 |
| WO | WO 2005/101017 | 10/2005 |
| WO | WO 2006/138629 | 12/2006 |
| WO | WO 2008/057083 | 12/2006 |
| WO | WO 2009/065414 | 5/2009 |
| WO | WO 2010/119295 | 10/2010 |
| WO | WO 2011/077129 | 6/2011 |
| WO | WO 2012/056232 | 5/2012 |
| WO | WO 2013/049410 | 4/2013 |
| WO | WO 2013/096451 | 6/2013 |
| WO | WO 2013/185180 | 12/2013 |
| WO | WO 2014/078374 | 5/2014 |
| WO | WO 2014/105985 | 7/2014 |
| WO | WO 2014/109927 | 7/2014 |
| WO | WO 2014/121031 | 8/2014 |
| WO | WO 2014/150170 | 9/2014 |
| WO | WO 2015/131169 | 9/2015 |
| WO | WO 2015/154052 | 10/2015 |
| WO | WO 2016/018978 | 2/2016 |
| WO | WO 2016/054114 | 4/2016 |
| WO | WO 2016/134365 | 8/2016 |
| WO | WO 2016/172485 | 10/2016 |
| WO | WO 2017/022315 | 2/2017 |
| WO | WO 2017/134274 | 8/2017 |
| WO | WO 2017/144903 | 8/2017 |
| WO | WO 2017/180735 | 10/2017 |
| WO | WO 2017/205694 | 11/2017 |
| WO | WO 2018/049001 | 3/2018 |

OTHER PUBLICATIONS

Mills et al. "Detecting monoclonal immunoglobulins in human serum using mass spectrometry." Methods. Jun. 15, 2015; 81:56-65 (Year: 2015).*

Rehder DS, Dillon TM, Pipes GD, Bondarenko PV. Reversed-phase liquid chromatography/mass spectrometry analysis of reduced monoclonal antibodies in pharmaceutics. J Chromatogr A. Jan. 13, 2006; 1102(1-2):164-75. (Year: 2006).*

Baenziger, "Structure of the oligosaccharide of human J chain," J. Biol. Chemistry, May 25, 1979, 254(10):4063-4071.

Cutillas, P. R. et al, Clinical Science 2003, 104, 483-490.

Hutchison, C. A. et al, Clinical Journal of the American Society of Nephrology 2008, 3, 1684-1690.

Johansen et al., "Role of J Chain in Secretory Immunoglobulin Formation," Scand. J. Immunology, Sep. 2000, 52(3):240-248.

Matheson et al., "Light chain-deficient mice produce novel multimerie heavy-chain-only IgA by faulty class switching," Int. Immunology, Aug. 2009, 21(8):957-966.

U.S. Appl. No. 16/930,790, filed Jul. 16, 2020, David L. Murray, Published.

Abca3:74m, "Understanding secondary antibodies" 2012, 12 pages, downloaded from http://docs.abcam.com/pdf/general/understanding_secondary_antibodies.pdf.

Abraham et al., "Characterization of free immunoglobulin light chains (LC) by mass spectrometry in light chain-associated (AL) amyloidosis," American Society of Hematology 43rd Annual Meeting, part 2, Orlando, Florida, USA, 98(11 Pt 2), p. 31b, Abstract#3722, Nov. 16, 2001.

Abraham et al., "Correlation of serum immunoglobulin free light chain quantification with urinary Bence Jones protein in light chain myeloma," Clin. Chem., 48(4):655-657, Apr. 2002.

Abraham et al., "Trimolecular complexes of lambda light chain dimers in serum of a patient with multiple myeloma," Clin Chem., 48(10):1805-1811, Oct. 2002.

(56) References Cited

OTHER PUBLICATIONS

Acera et al., "Changes in tear protein profile in keratoconus disease," Eye, 25(9):1225-33, Sep. 2011.
Adamczyk et al., "Profiling of polyclonal antibody light chains by liquid chromatography/electrospray ionization mass spectrometry," Rapid Commun Mass Spectrom., 14:49-51, 2000.
Adamczyk et al., "Papain digestion of different mouse IgG subclasses as studied by electrospray mass spectrometry," J Immun Methods., 237:95-104, 2000.
Aisina and Mukhametova, "Structure and Function of Plasminogen/Plasmin System," Russian Journal of Bioorganic Chemistry, 40(6):590-605, Nov. 2014.
Alge et al., "Proteomic Analysis of Plasma Exosome-Associated Proteins Reveals That Differences in Kappa: Lambda Ratios Predict Severe Acute Graft-Versus-Host Disease Early After Allogeneic Hematopoietic Stem Cell Transplantation," Blood., 1278, Nov. 2010.
Alldridge et al., "Proteome profiling of breast tumors by gel electrophoresis and nanoscale electrospray ionization mass spectrometry," J. Proteome. Res., 7(4):1458-1469, Apr. 2008.
Anonymous: "KappaSelect LambdaFabSelect," Data File 28-9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.
Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.
Attealnnannan and Levinson et al., "Understanding and Identifying monoclonal gammopathies," Clinical Chemistry, Aug. 2000, 46(8B):1230-1238.
Aucouturier et al., "Monoclonal Ig L chain and L chain V domain fragment crystallization in myeloma-associated Fanconi's syndrome" J. Immunol., 150(8 Pt 1):3561-3568, Apr. 1993.
Aucouturier et al., "Monoclonal immunoglobulin light chains associated to Fanconi's syndrome," Monoclonal Gammopathies and the Kidney, 2003, 87-92.
Awad et al., "Analyses of cerebrospinal fluid in the diagnosis and monitoring of multiple sclerosis," J Neuroimmunol., 219(1-2): 1-7, Epub Sep. 25, 2009.
Balakrishnan et al., "Differential proteomic analysis of synovial fluid from rheumatoid arthritis and osteoarthritis patients," Clin. Proteomics., 11(1):1, 2014.
Baldini et al., "Correspondence between salivary proteomic pattern and clinical course in primary Sjögren syndrome and non-Hodgkin's lymphoma: a case report," Journal of translational medicine, 9(1):188, Dec. 2011.
Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.
Barnidge et al., "Monitoring free light chains in serum using mass spectrometry," Clinical Chemistry and Laboratory Medicine (CCLM). ISSN (Online) 1437-4331, ISSN (Print) 1434-6621, DOI: 10.1515/cclm-2015-0917, Feb. 2016.
Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.
Barnidge et al., "Phenotyping polyclonal kappa and lambda light chain molecular mass distributions in patient serum using mass spectrometry," J Proteome Res., 13(11):5198-5205, Epub Aug. 26, 2014.
Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.
Barnidge et al., "Using mass spectrometry to monitor monoclonal immunoglobulins in patients with a monoclonal gammopathy," J Proteome Res., 13(3):1419-1427, Epub Feb. 11, 2014.
Barnidge, "Monitoring specific IgG tryptic peptides in multiple myeloma using the TripleTOFtm 5600 System," AB SCIEX Annual Users Meeting at ASMS, May 20, 2012, 28 slides.
Barratt et al., "Urine proteomics: the present and future of measuring urinary protein components in disease," CMAJ, 177(4):361-368, Aug. 2007.
Bastian et al., "Intra- and interchain disulfide bridges of the human J chain in secretory immunoglobulin A," Biol. Chem. Hoppe Seyler., 373(12):1255-63, Dec. 1992.
Beck et al., "Characterization of therapeutic antibodies and related products," Anal. Chem., 85(2):715-736, Jan. 2013.
Bennett et al., "Monitoring papain digestion of a monoclonal antibody by electrospray ionization mass spectrometry," Analytical Biochemistry., 245:17-27,1997.
Berg et al., "Mass spectrometry based proteomic analysis identifies two distinct types of cutaneous amyloidosis," Mod Pathol., vol. 22; p100A, 2009.
Bergen et al., "Characterization of amyloidogenic immunoglobulin light chains directly from serum by on-line immunoaffinity isolation," Biomedical Chromatography, 18(3):191-201, Apr. 1, 2004.
Bergon et al., "Linearity and detection limit in the measurement of serum M-protein with the capillary zone electrophoresis system Capillarys," Clinical Chemistry and Laboratory Medicine, 43:721-723, 2005.
Bermudez-Crespo et al., "A better understanding of molecular mechanisms underlying human disease," Proteomics Clinical Applications, 1:983-1003, 2007.
Biosis accession No. PREV200200151435, 2 pages, Nov. 2001 Abstract only.
Biosis accession No. PREV201100424453, 2 pages, Nov. 2010 Abstract only.
Bois et al., "Cutaneous amyloidosis: mass spectrometry based proteomic analysis reveals diverse etiology associated with unique histopathological features," Mod Pathol., 26:320A-321A, Feb. 2013.
Boissinot et al., "Up-Regulation of Anti-Inflammatory, STAT3-Activating Hepatocyte Growth Factor and Interleukin-11 in Polycythemia Vera Is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.
Bondarenko et al., "Mass measurement and top-down HPLC/MS analysis of intact monoclonal antibodies on a hybrid linear quadrupole ion trap-orbitrap mass spectrometer," J Am Soc Mass Spectrometry., 20:1415-1424, 2009.
Bourell et al., "Electrospray ionization mass spectrometry of recombinantly engineered antibody fragments," Anal Chem., 66:2088-2095, 1994.
Bradwell et al., "Highly sensitive, automated immunoassay for immunoglobulin free light chains in serum and urine," Clin Chem., 47(4):673-680, Apr. 2001.
Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40):16190-16195, Oct. 2012.
Brochet et al., "IMGT/V-QUEST: the highly customized and integrated system for IG and TR standardized V-J and V-D-J sequence analysis," Nucleic Acids Res., 36(Web Server issue):W503-W508, Epub May 24, 2008.
Butler et al., "Immunoglobulins, antibody repertoire and B cell development," Dev Comp Immunol., 33(3):321-333, Epub Sep. 18, 2008.
Chen et al., "Characterization of protein therapeutics by mass spectrometry: recent developments and future directions," Drug Discovery Today., 16:58-64, 2011.
Cheung et al., "A proteomics approach for the identification and cloning of monoclonal antibodies from serum," Nature Biotechnology., 30:447-452, 2012.
Chevreux et al., "Fast analysis of recombinant monoclonal antibodies using IdeS proteolytic digestion and electrospray mass spectrometry," Analytical Biochemistry, 415(2):212-214, Aug. 2011.
Chiasserini et al., "CSF proteome analysis in multiple sclerosis patients by two-dimensional electrophoresis," Eur. J. Neurol., 15(9):998-1001, Sep. 2008.

(56) References Cited

OTHER PUBLICATIONS

Chow et al., "Serum immune-related proteins are differentially expressed during hibernation in the American black bear," PLoS One, 8(6), 2013.
Chung et al., "Thermodynamic stability of a kappaI immunoglobulin light chain: relevance to multiple myeloma," Biophys. J., 88(6):4232-4242, Jun. 2005.
Cohen et al., "β-Elimination and peptide bond hydrolysis: two distinct mechanisms of human IgG1 hinge fragmentation upon storage," Journal of the American Chemical Society, 129(22):6976-7, Jun. 2007.
Cohen., "Antibody structure," J Clin Path., 28 Suppl, 6:1-7, 1975.
Cordoba et al., "Non-enzymatic hinge region fragmentation of antibodies in solution," J Chromatography B., 818:115-121, 2005.
Coriu et al., "A molecular basis for nonsecretory myeloma," Blood, 104(3):829-831, Aug. 2004.
Cretu, "Identification and Validation of Candidate Soluble Biomarkers for Psoriatic Arthritis Using Quantitative Proteomics (Doctoral dissertation)", 2015.
D'Aguanno et al., "Differential cerebro spinal fluid proteome investigation of Leber hereditary optic neuropathy (LHON) and multiple sclerosis," 193(1-2):156-160, Dec. 2007.
Dai Y, Hu C, Huang Y, Huang HY, Liu J, Lv T. A proteomic study of peripheral blood mononuclear cells in systemic lupus erythematosus. Lupus. Sep. 2008;17(9):799-804.
Damoc et al., "High resolution proteome analysis of cryoglobulins using Fourier transform-ion cyclotron resonance mass spectrometry," Proteomics, 3(8):1425-1433, Aug. 2003.
De Costa et al., "Sequencing and Quantifying IgG Fragments and Antigen-Binding Regions by Mass Spectrometry" Journal of Proteome Research, 9:2937-2945, Epub Apr. 14, 2010.
De Lorenzi et al., "Urokinase links plasminogen activation and cell adhesion by cleavage of the RGD motif in vitronectin," EMBO reports, 17(7):982-98, Jul. 2016.
Dear et al., "Acquired dysfibrinogenemia caused by monoclonal production of immunoglobulin lambda light chain," Haematologica., 92(11):e111-7, Nov. 2007.
Dekker et al., "An Antibody-Based Biomamarker Discovery Method by Mass Spectrometry Sequencing of Complementarity Determining Regions," Analytical and Bioanalytical Chemistry, 399:1081-1091, 2011.
Deng et al., "Plasma proteomic analysis of pancreatic cancer by 2-dimensional gel electrophoresis," Pancreas, 34(3):310-7, Apr. 2007.
Deshpande et al., "GlycoSpectrumScan: fishing glycopeptides from MS spectra of protease digests of human colostrum sIgA," Journal of proteome research, 9(2):1063-75, Feb. 2010.
Dillon et al., "Optimization of a reversed-phase high-performance liquid chromatography/mass spectrometry method for characterizing recombinant antibody heterogeneity and stability," J. Chromatogr. A., 1120(1-2):112-20, Jul. 2006.
Dogan et al., "Leukocyte Chemotactic Factor 2 Amyloidosis: A Novel Type of Amyloidosis That Mimics AL Amyloidosis," presented at the United States and Canadian Academy of Pathology Annual Meeting, Mar. 2009, 1 page.
Drożdż et al., "Immunoglobulin cleavage by hypochlorous acid treatment," Clinica. Chimica. acta., 236(2):155-60, May 1995.
Ellias et al., "Proteomic analysis of saliva identifies potential biomarkers for orthodontic tooth movement," The Scientific World Journal, 2012.
Faca et al., "Innovative proteomic approaches for cancer biomarker discovery," Biotechniques, 43(3):279-283, Sep. 2007.
Fan et al., "A single proteolytic cleavage within the lower hinge of trastuzumab reduces immune effector function and in vivo efficacy," Breast Cancer Research, Aug. 2012, 14(4):R116.
Fan et al., "Identification of Niemann-Pick C1 disease biomarkers through sphingolipid profiling," J. Lipid. Res., 54(10):2800-2814, Oct. 2013.
Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.
Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.
Frangione, B., "Structure of Human Immuniglobulins and their Variants" B. Benacerraf (ed) Immunogenetics and Immunodeficiency, 1-53, 1975.
Gadgil et al., "The LC/MS analysis of glycation of IgG molecules in sucrose containing formulations," Jornal of Pharmaceutical Sciences, 96(10):2607-2621, Oct. 2007.
Gebski et al., "Affinity chromatography applications with single-domain antibodies," Bioprocess International., Aug. 1, 2013, Retrieved from the Internet: URL: http://www.bioprocessintl.com/2013/affinity-chromatography-applications-with-single-domain-antibodies-345480/ Retrieved on Sep. 22, 2017.
GenBank Accession AAA59107, "immunoglobulin lambda light chain C2 region, partial [*Homo sapiens*]," May 4, 2000, 2 pages.
Ghafouri et al., "Newly identified proteins in human nasal lavage fluid from non-smokers and smokers using two-dimensional gel electrophoresis and peptide mass fingerprinting," Proteomics: International Edition, 2(1):112-20, Jan. 2002.
Goetze et al., "High-mannose glycans on the Fc region of therapeutic IgG antibodies increase serum clearance in humans," Glycobiology, 21(7):949-59, Jul. 2011.
Grazio et al., "Differential expression of proteins with heparin affinity in patients with rheumatoid and psoriatic arthritis: a preliminary study," Clin. Exp. Rheumatol., 31(5):665-671, 2013.
Gucinski et al., "Evaluation of intact mass spectrometry for the quantitative analysis of protein therapeutics," Anal. Chem., 84(18):8045-8051, Sep. 2012.
Hagman et al., "Absolute quantification of monoclonal antibodies in biofluids by liquid chromatography-tandem mass spectrometry," Analytical Chemistry, 80(4):1290-1296, Feb. 15, 2008.
Hagmann et al., "Characterization of the F(ab')2 fragment of a murine monoclonal antibody using capillary isoelectric focusing and electrospray ionization mass spectrometry," J Chromatography A., 816:49-58, 1998.
Hanash et al., "Mining the plasma proteome for cancer biomarkers," Nature, 452(7187)571-579, Apr. 2008.
Haraldsson et al., "Determination of kappa and lambda light chains in serum immunoglobulins G, A and M," Ann Clin Biochem., 28 (Pt 5):461-466, Sep. 1991.
Hess et al., "Immunoglobulin cleavage by the streptococcal cysteine protease IdeS can be detected using protein G capture and mass spectrometry," Journal of microbiological methods, Aug. 2007, 70(2):284-91.
Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.
Hieter et al., "Clustered arrangement of immunoglobuling constant region genes in man," Nature, 294:536-540, 1981.
Hill et al., "Serum free light chains: an alternative to the urine Bence Jones proteins screening test for monoclonal gammopathies," Clin. Chem., 52(9):1743-1748, Sep. 2006.
Holding et al., "Use of serum free light chain analysis and urine protein electrophoresis for detection of monoclonal gammopathies," Clin. Chem. Lab. Med., 49(1):83-88, Jan. 2011.
Hsieh et al., "Elucidation of potential bortezomib response markers in multiple myeloma patients," Journal of Pharmaceutical and Biomedical Analysis, 49:115-122, 2009.
Huang et al., "Site-specific glycosylation of secretory immunoglobulin A from human colostrum. Journal of proteome research," 14(3):1335-49, Mar. 2015.
Huse et al., "Purification of antibodies by affinity chromatography," Journal of biochemical and biophysical methods, 51(3):217-31, May 2002.

(56) References Cited

OTHER PUBLICATIONS

Hutchison et al., "The pathogenesis and diagnosis of acute kidney injury in multiple myeloma," Nature Reviews Nephrology, Jan. 2012, 8:43-51.
Iannaccone et al., "Retinal pigment epithelium and microglia express the CD5 antigen-like protein, a novel autoantigen in age-related macular degeneration," Exp Eye Res., 155:64-74, 2017.
International Preliminary Report on Patentability International in Application No. PCT/US2018/050846 dated Mar. 26, 2020, 9 pages.
International Search Report & Written Opinion in International Application No. PCT/US2018/050846 dated Nov. 18, 2018, 16 pages.
Ito and Arata, "Proton nuclear magnetic resonance study on the dynamics of the conformation of the hinge segment of human G1 immunoglobulin," Biochemistry, Nov. 1985, 24(23):6467-74.
Jagannath et al., "Value of serum free light chain testing for the diagnosis and monitoring of monoclonal gammopathies in hematology," Clin Lymphoma Myeloma, 7(8):518-523, Sep. 2007.
Jemal et al., "Cancer statistics, 2003," CA Cancer J Clin., 53(1):5-26, Jan.-Feb. 2003.
Johnson et al., "Cation exchange-HPLC and mass spectrometry reveal C-terminal amidation of an IgG1 heavy chain," Anal. Biochem., 360(1):75-83, Jan. 2007.
Jones et al., "A protocol for 'enhanced pepsin digestion': a step by step method for obtaining pure antibody fragments in high yield from serum," J of Immunol Methods., 275:239-250, 2003.
Joosten et al., "The production of antibody fragments and antibody fusion proteins by yeasts and filamentous fungi," Microbial Cell Factories., 2:1, 15 pages, 2003.
Kabat et al., "An electrophoretic study of the protein components in cerebrospinal fluid and their relationship to the serum proteins," J Clin Invest., 21(5):571-577, Sep. 1942.
Kalaga et al., "Unexpected presence of polyreactive catalytic antibodies in IgG from unimmunized donors and decreased levels in rheumatoid arthritis," J. Immunol., 155(5):2695-2702, Sep. 1995.
Kaltashov et al., "Advances and challenges in analytical characterization of biotechnology products: Mass spectrometry-based approaches to study properties and behavior of protein therapeutics," Biotechnology Advances., 30:210-222, 2012.
Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology., 144(5):705-715, 2008.
Kaplan et al., "Immunoglobulin free light chain dimers in human diseases," The Scientific World Journal, 11:726-735, Mar. 2011.
Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3):335-341, Mar. 2008.
Katzmann et al., "Serum reference intervals and diagnostic ranges for free kappa and free lambda immunoglobulin light chains: relative sensitivity for detection of monoclonal light chains," Clin. Chem., 48(9):1437-44, Sep. 2002.
Kim et al., "Prediction of Response to Sorafenib in Hepatocellular Carcinoma: A Putative Marker Panel by Multiple Reaction Monitoring-Mass Spectrometry (MRM-MS)," Mol. Cell Proteomics., 16(7):1312-132, 2017.
Kiselar et al., "Direct Identification of Protein Epitopes by Mass Spectrometry Without Immobilization of Antibody and Isolation of Antibody-Peptide Complexes," Analytical Chemistry, May 1999, 71(9):1792-1801.
Kissel and Mendell, "Neuropathies associated with monoclonal gammopathies," Neuromuscular disorders, Jan. 1996, 6(1):3-18.
Kleennann et al., "Characterization of IgG1 immunoglobulins and peptide-Fc fusion proteins by limited proteolysis in conjunction with LC-MS," Analytical Chemistry, 80(6):2001-2009, Mar. 2008.
Koh et al., "Characterization of exosomes from body fluids of dairy cows," J. Anim. Sci., 95(9):3893-3904, 2017.
Kohlhagen, "Using Maldi-Tof Ms to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312_53747.pdf>, MSACL 2015 US: Preliminary Conference Program, San Diego, CA, Mar. 28-Apr. 1, 2015, 2 pages.
Kolialexi et al., "Plasma biomarkers for the identification of women at risk for early-onset preeclampsia," Expert Rev. Proteomics., 14(3):269-276, 2017.
Koomen et al., "Proteomic contributions to personalized cancer care," Molecular & Cellular Proteomics, 7.10:1780-1794, 2008.
Kowarik et al., "The cerebrospinal fluid immunoglobulin transcriptome and proteome in neuromyelitis optica reveals central nervous system-specific B cell populations," J Neuroinflammation., 12:19, Jan. 28, 2015.
Kragten et al., "Site-specific analysis of the N-glycans on murine polymeric immunoglobulin A using liquid chromatography/electrospray mass spectrometry," Journal of Mass Spectrometry, 30(12):1679-86, Dec. 1995.
Kroon et al., "Identification of sites of degradation in a therapeutic monoclonal antibody by peptide mapping," Pharmaceutical Research., 9:1386-1393, 1992.
Kurokawa et al., "Macrophage-derived AIM is endocytosed into adipocytes and decreases lipid droplets via inhibition of fatty acid synthase activity," Cell metabolism, 11(6):479-92, Jun. 2010.
Kyle et al., "Criteria for the classification of monoclonal gammopathies, multiple myeloma and related disorders: a report of the International Myeloma Working Group," Br. J. Haematol., 121(5):749-757, Jun. 2003.
Ladwig et al., "Quantification of serum IgG subclasses by use of subclass-specific tryptic peptides and liquid chromatography-tandem mass spectrometry," Clin Chem., 60(8):1080-1088, May 5, 2014.
Landgren et al., "Monoclonal gammopathy of undetermined significance (MGUS) consistently precedes multiple myeloma: a prospective study" Blood, 113(22):5412-5417, May 28, 2009.
Lavatelli et al., "A novel approach for the purification and proteomic analysis of pathogenic immunoglobulin free light chains from serum," Biochimica rt Biophysica Acta., 1814(3):409-419, Mar. 2011.
Lebeau et al., "Generalized crystal-storing histiocytosis associated with monoclonal gammopathy: molecular analysis of a disorder with rapid clinical course and review of the literature," Blood., 100:1817-1827, 2002.
Lee et al., "Relationship between Group-Specific Component Protein and the Development of Asthma," American journal of respiratory and critical care medicine 184(5):528-536, 2011.
Lefranc, "IMGT, the International ImMunoGeneTics Information System," Cold Spring Harb Protoc., 2011(6):595-603, Jun. 1, 2011.
Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.
Leung et al., "A novel and rapid approach to protein expression profiling of cerebrospinal fluid (CSF) from medulloblastoma patients using functionalized magnetic beads, AnchorChipTM technology, MALDI-TOf and MALDI-TOF/TOF mass spectrometry," 33rd Meeting of the Society of Neuroscience, 751.3, Nov. 2003.
Leung et al., "Monoclonal gammopathy of renal significance: when MGUS is no longer undetermined or insignificant," Blood, 120:4292-4295, 2012.
Li et al., "General LC-MS/MS method approach to quantify therapeutic monoclonal antibodies using a common whole antibody internal standard with application to preclinical studies," Analytical Chemistry, 84:1267-1273, 2012.
Li et al., "Simultaneous analysis of multiple monoclonal antibody biotherapeutics by LC-MS/MS method in rat plasma following cassette-dosing," AAPS J., 15(2):337-346, Epub Dec. 12, 2012.
Lill et al., "Microwave-assisted proteomics," Mass spectrometry reviews, 26(5):657-71, Sep. 2007.

(56) References Cited

OTHER PUBLICATIONS

Lim et al., "Identification and Location of a Cysteinyl Post-translational Modification in an Amyloidogenic kappal Light Chain Protein by Electrospray Ionization and Matrix-Assisted Laser Desorption/Ionization Mass Spectrometry," Analytical Biochemistry, Aug. 2001, 295:45-56.
Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.
Liu et al., "Analysis of plasma proteome from cases of the different traditional Chinese medicine syndromes in patients with chronic hepatitis B," Journal of Pharmaceutical and Biomedical Analysis, 59:173-178, 2012.
Liu et al., "Quantitation of a recombinant monoclonal antibody in monkey serum by liquid chromatography-mass spectrometry," Anal Biochem., 414(1):147-153, Epub Mar. 8, 2011.
Lokamani et al., "Gelsolin and ceruloplasmin as potential predictive biomarkers for cervical cancer by 2D-DIGE proteomics analysis," Pathology & Oncology Research, 20(1):119-29, Jan. 2014.
Lu et al., "Detection of abundant proteins in multiple myeloma cells by proteomics," J Proteomics Bioinform., 3(1):005-009, 2010.
Lu et al., "LC-MS Analysis of Polyclonal Human Anti-Neu5Gc Xeno-Autoantibodies Immunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.
Marien et al., "Detection of monoclonal proteins in sera by capillary zone electrophoresis and free light chain measurements," Clin. Chem., 48(9):1600-1601, Sep. 2002.
Markowitz, "Dysproteinemia and the Kidney," Advances in Anatomic Pathology, Jan. 2004, 11:49-63.
Mazur et al., "A platform for characterizing therapeutic monoclonal antibody breakdown products by 2D chromatography and top-down mass spectrometry," The AAPS journal, 14(3):530-41, Sep. 2012.
McBride et al., "Chromosomal location of human kappa and lambda immunoglobulin light chain constant region genes, " J Exp Med., 155(5):1480-1490, May 1, 1982.
Merlini and Palladini, "Differential diagnosis of monoclonal gammopathy of undetermined significance" Hematology, 595-603, 2012.
Micallef, J. et al, Journal of Hennatology & Oncology 2010, 3, 11 pages.
Mills et al., "Using mass spectrometry to quantify rituximab and perform individualized immunoglobulin phenotyping in ANCA-associated vasculitis," Analytical chemistry, 88(12):6317-25, Jun. 2016.
Minnura et al., "Contrasting glycosylation profiles between Fab and Fc of a human IgG protein studied by electrospray ionization mass spectrometry," J. Immunol. Methods., 326(1-2):116-26, Sep. 2007.
Mischak et al., "Urinary proteome analysis using capillary electrophoresis coupled to mass spectrometry: a powerful tool in clinical diagnosis, prognosis and therapy evaluation," Journal of Medical Biochemistry, Oct. 2009, 28(4):223-234.
Mitchell et al., "Alterations in the bovine bronchoalveolar lavage proteome induced by dexamethasone," Veterinary immunology and immunopathology, 118(3-4):283-93, Aug. 2007.
Moh et al., "Site-specific N-glycosylation of recombinant pentameric and hexameric human IgM," Journal of the American Society for Mass Spectrometry, 27(7):1143-55, Apr. 2016.
Mohr et al., "High-efficiency nano- and micro-HPLC—high-resolution Orbitrap-MS platform for top-down proteomics," Proteomics., 10(20):3598-3609, Oct. 2010.
Mukhopadhyay et al., "A tribute to Frank Anscombe and random central limit theorem from 1952," Sequential Analysis, 31(3): 265-277, 2012.
Murphy et al., "Characterization of systemic amyloid deposits by mass spectrometry," Methods Enzymol., 412:48-62, 2006.
Murray et al., "Characterization of immunoglobulin by mass spectrometry with applications for the clinical laboratory," Crit. Rev. Clin Lab. Sci., 50(4-5):91-102, Jul.-Oct. 2013.
Nasr et al., "Immunotactoid glomerulopathy: clinicopathologic and proteomic study," Nephrol Dial Transplant., 27(11):4137-4146, Epub Aug. 7, 2012.
Obermeier et al., "Matching of oligoclonal immunoglobulin transcriptomes and proteomes of cerebrospinal fluid in multiple sclerosis," Nat Med., 14(6):688-693, Epub May 18, 2008.
Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.
Okamoto et al., "Proteome analysis of bronchoalveolar lavage fluid in chronic hypersensitivity pneumonitis," Allergology International, 61(1):83-92, Jan. 2012.
Oruc et al., "IgA structure variations associate with immune stimulations and IgA mesangial deposition," Journal of the American Society of Nephrology, 27(9):2748-61, Sep. 2016.
Pabst et al., "A microarray-matrix-assisted laser desorption/ionization-mass spectrometry approach for site-specific protein N-glycosylation analysis, as demonstrated for human serum immunoglobulin M (IgM)," Molecular & Cellular Proteomics, 14(6):1645-56, Jun. 2015.
Pang et al., "Biomarker discovery in urine by proteomics," Journal of Proteome Research, 1:161-169, Epub Feb. 16, 2002.
Persson et al., "Development of Mass Spectrometry Based Techniques for the Identification and Determination of Compositional Variability in Recombinant Polyclonal Antibody Products," Analytical Chemistry, Sep. 2010, 82(17): 7274-7282.
Piehler et al., "Quantitation of serum free light chains in combination with protein electrophoresis and clinical information for diagnosing multiple myeloma in a general hospital population," Clin. Chem., 54(11):1823-1830, Nov. 2008.
Qin et al., "Development of a "reverse capture" autoantibody microarray for studies of antigen-autoantibody profiling," Proteomics., 6(10):3199-209, May 2006.
Radovic, V. V., "Recommendations for Use of Free Light Chain Assay in Monoclonal Gammopathies" Journal of Medical Biochemistry, 29:1-8, 2010.
Rajkumar et al., "Advances in the diagnosis, classification, risk stratification, and management of monoclonal gammopathy of undertermined significance: implications for recategorizing disease entities in the presence of evolving scientific evidence," Mayo Clinic Proceedings., 85:945-948, 2010.
Reid et al., "Rapid whole monoclonal antibody analysis by mass spectrometry: An ultra scale-down study of the effect of harvesting by centrifugation on the post-translational modification profile," Biotechnology and Bioengineering, 107(1):85-95, Sep. 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," J Chromatography A., 1179:198-204, 2008.
Roberts et al., "An Integrated Strategy for Structural Characterization of the Protein and Carbohydrate Components of Monoclonal Antibodies: Application to Anti-Respiratory Syncytial Virus Mab," Analytical Chemistry, Oct. 1995, 67(20):3613-3625.
Rodriguez et al., "Immunoglobulin derived depositions in the nervous system: novel mass spectrometry application for protein characterization in formalin-fixed tissues," Lab Invest., 88(10):1024-1037, Epub Aug. 18, 2008.
Rosati et al., "Exploring an orbitrap analyzer for the characterization of intact antibodies by native mass spectrometry," Angew. Chem. Int. Ed. Engl., 51(52):12992-12996, Dec. 2012.
Ruan et al., "Strategy and its implications of protein bioanalysis utilizing high-resolution mass spectrometric detection of intact protein," Anal. Chem., 83(23):8937-8944, Dec. 2011.
Salinas et al., "Buffer-dependent fragmentation of a humanized full-length monoclonal antibody," Journal of pharmaceutical sciences, 99(7):2962-74, Jul. 2010.
Sandoval et al., "Rapid removal of N-linked oligosaccharides using microwave assisted enzyme catalyzed deglycosylation," International Journal of Mass Spectrometry, 259(1-3):117-23, Jan. 2007.

(56) References Cited

OTHER PUBLICATIONS

Sanjurjo et al., "AIM/CD5L: a key protein in the control of immune homeostasis and inflammatory disease," J. Leukoc. Biol., 98(2):173-184, Aug. 2015.
Sarrias et al., "Biochemical characterization of recombinant and circulating human Spa," Tissue antigens, Apr. 2004, 63(4):335-44.
Schaefer et al., "Residual serum monoclonal protein predicts progression-free survival in patients with previously untreated multiple myeloma," Cancer., 116:640-646, 2010.
Sethi et al., "Mass spectrometry-based proteomic diagnosis of renal immunoglobulin heavy chain amyloidosis," Clin J Am Soc Nephrol., 5:2180-2187, 2010.
Shaheen et al., "Multiple Myeloma and Immunosecretory Disorders: An Update," Advances in Anatomic Pathology, Jul. 2008, 15(4):196-210.
Sikkink et al., "Biochemical and Aggregation Analysis of Bence Jones Proteins From Different Light Chain Diseases," Amyloid, Mar. 2008, 15:29-39.
Singh et al., "Cerebrospinal-fluid-derived immunoglobulin G of different multiple sclerosis patients shares mutated sequences in complementarity determining regions," Mol Cell Proteomics, 12(12):3924-3934, Epub Aug. 22, 2013.
Skriner et al., "Association of citrullinated proteins with synovial exosomes," Arthritis & Rheumatism: Official Journal of the American College of Rheumatology, Dec. 2006, 54(12):3809-14.
Sloane et al., "Proteomic analysis of sputum from adults and children with cystic fibrosis and from control subjects. American journal of respiratory and critical care medicine," Dec. 2005, 172(11):1416-26.
Song et al., "Characterization of N-terminal processing of group VIA phospholipase A2 and of potential cleavage sites of amyloid precursor protein constructs by automated identification of signature peptides in LC/MS/MS analyses of proteolytic digests," J Am Soc Mass Spectrom., 15(12):1780-1793, Dec. 2004.
Stoop et al., "Quantitative MALDI-FT-ICR analysis of cerebrospinal fluid of relapsing-remitting and primary progressive multiple sclerosis patients," Multiple Sclerosis., 15(9):S83, Sep. 2009.
Stubbs et al., "Anti-neurofilament antibodies in neuropathy with monoclonal gammopathy of undetermined significance produce experimental motor nerve conduction block," Acta Neuropathology., 105:109-116, 2003.
Sun et al., "Immunoglobulin genes and diversity: what we have learned from domestic animals," J Anim Sci Biotechnol., 3(1):18, Jun. 20, 2012.
Sun et al., "Preparation and mass spectrometric study of egg yolk antibody (IgY) against rabies virus," Rapid communications in mass spectrometry, 15(9):708-12, May 2001.
Theis et al., "Immunoglobulin Light Chain Gene Constant Region Is an Invariable Part of Amyloid Deposits in AL Amyloidosis," Blood, 112(11):3128, Nov. 16, 2008.
Theis et al., "Mass spectrometry based proteomic analysis of AL amyloidosis: Immunoglobulin Light Chain Gene Constant Region Is an Invariable Part of Amyloid Deposits and provides valuable diagnostic target," presented at the United States and Canadian Academy of Pathology Annual Meeting, Mar. 2009, 1 page.
Thermo Scientific, "MelonTM Gel IgG Spin Purification Kit" [online], 2011 [retrieved on Aug. 6, 2015]. Retrieved from the Internet: <URL: https://tools.lifetechnologies.com/content/sfs/manuals/MAN0011513_Melon_Gel_1gG_Spin_Purifi_UG.pdf>, 4 pages.
Thurgood et al., "An Immunodominant La/SSB autoantibody proteome derives from public clonotypes," Clinical and Experimental Immunology., 174:237-244, Oct. 6, 2013.
Tissot et al., "IgM Are Associated to Sp Alpha (CD5 Antigen-Like)," Electrophoresis, 23(7-8):1203-1206, Apr. 2002.
VanDuijn et al., "Immune responses are characterized by specific shared immunoglobulin peptides that can be detected by proteomic techniques," Journal of Biological Chemistry, 285:29247-29253, Jul. 8, 2010.
Vase et al., "A57 Proteomic profiling of pretreatment serum from HIV-infected patients identifies candidate markers predictive of lymphoma development," AIDS, 2016, 30(12):1889-1898.
Verheesen et al., "Beneficial properties of single-domain antibody fragments for application in immunoaffinity purification and immuno-perfusion chromatography," Biochim Biophys Acta., 1624(1-3):21-28, Dec. 5, 2003.
Vlasak and Ionescu, 2011, mAbs 3:253-263.
Vrana et al., "Classification of amyloidosis by laser microdissection and mass spectrometry-based proteomic analysis in clinical biopsy specimens," Blood, 114(24):4957-4960, Dec. 2009.
Vrana et al., "Amyloidosis typing based on Laser Microdissection and Mass Spectrometry of Paraffin-Embedded Tissue Biopsies" Companion to Peripheral Neuropathy, pp. 347-349, 2010.
Vrana et al., "Classification of Amyloidosis in Fat Aspiration Specimens Using Mass Spectrometry Based Proteomics," presented at the United States and Canadian Academy of Pathology Annual Meeting, Mar. 2009, 1 page.
Vrana et al., "Diagnosis and Classification of Amyloidosis in Abdominal Subcutaneous Fat Aspiration Specimens Using Mass Spectrometry Based Proteomics," Blood, 112(11):2710, Nov. 16, 2008.
Vrana et al., "Diagnosis and Typing of Cardiac Amyloidosis in Routine Clinical Specimens by Mass Spectrometry Based Proteomic Analysis," presented at the United States and Canadian Academy of Pathology Annual Meeting, Mar. 2009, 1 page.
Wagner-Rousset et al., "The way forward, enhanced characterization of therapeutic antibody glycosylation: comparison of three level mass spectrometry-based strategies," Journal of Chromatography B, 872(1-2):23-37, Sep. 2008.
Wang et al., "Construction of a Multiple Myeloma Diagnostic Model by Magnetic Bead-Based MALDI-TOF Mass Spectrometry of Serum and Pattern Recognition Software" Anatomical Record, 292:604-610, 2009.
Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.
Wang et al., "Discovery of potential colorectal cancer serum biomarkers through quantitative proteomics on the colonic tissue interstitial fluids from the AOM-DSS mouse model," J. Proteomics, 2016, 132:31-40.
Wang et al., "Molecular basis of assembly and activation of complement component C1 in complex with immunoglobulin G1 and antigen," Molecular cell, 63(1):135-45, Jul. 2016.
Wang et al., "Structural Characterization of a Recombinant Monoclonal Antibody by Electrospray Time-Of-Flight Mass Spectrometry," Pharmaceutical Research, Aug. 2005, 22(8):1338-1349.
Whiteaker et al., "Sequential multiplexed analyte quantification using peptide immunoaffinity enrichment coupled to mass spectrometry," Mol Cell Proteomics., 11(6):10.1074/mcp.M111.015347, 2012,10 pages.
Willrich et al., "Quantitation of infliximab using clonotypic peptides and selective reaction monitoring by LC-MS/MS," International Immunopharmacology., 28(1):513-520, Sep. 1, 2015.
Willrich et al., "Serum infliximab quantitation by LC-MS/MS in patients treated for inflammatory disorders," Gastroenterology AGA Abstracts., Sal252, May 1, 2014, Retrieved from the internet: URL:https://ac.els-cdn.com/SOO16508514608568/1-S2.0-S0016508514608568-mai n.pdf?_ ti d=e58e3b4c-caOa-lle7-96b2-OOOOOaabOf6b&acdnat=1510753563_ 74ab7a6bOb5f976b8c948a995d894fce, Retrieved on Nov. 15, 2017, Abstract Only.
Wine, Y. et al. Molecular deconvolution of the monoclonal antibodies that comprise the polyclonal serum response, PNAS vol. 110, No. 8, pp. 2993-2998 (Year: 2013).
Xu et al., "Discovery and identification of serum potential biomarkers for pulmonary tuberculosis using iTRAQ-coupled two-dimensional LC-MS/MS," Proteomics, 2014, 14(2-3):322-331.
Yamazaki et al., "A proteolytic modification of AIM promotes its renal excretion," Scientific Reports, 6:38762, Dec. 2016.

(56) References Cited

OTHER PUBLICATIONS

Yin et al., "Protein biomarkers of new-onset cardiovascular disease: prospective study from the systems approach to biomarker research in cardiovascular disease initiative," Arterioscler. Thromb. Vasc. Biol., 2014, 34(4):939-945.
Zhang et al., "Characterization of variable regions of monoclonal antibodies by top-down mass spectrometry," Anal Chem., 79(15):5723-5729, 2007.
Zhang et al., "Proteomic analysis of plasma in adult active pulmonary tuberculosis patients with diabetes mellitus," The FASEB Journal, Apr. 2015, 29(1_supplement):275-7.
Zhaoyu et al., "Alteration of DBP levels in CSF of patients with MS by proteomics analysis," Cell Mol. Neurobiol., 29(2):203-210, Mar. 2009.
Zhong et al., "Microwave-assisted acid hydrolysis of proteins combined with liquid chromatography MALDI MS/MS for protein identification," Journal of the American Society for Mass Spectrometry, Apr. 2005, 16(4):471-81.
Zhong et al., "Protein sequencing by mass analysis of polypeptide ladders after controlled protein hydrolysis," Nature biotechnology, Oct. 2004, 22(10):1291-6.
Zhou et al., "Quantitative analysis of N-linked glycoproteins in tear fluid of climatic droplet keratopathy by glycopeptide capture and iTRAQ," Journal of proteome research, Apr. 2009, 8(4):1992-2003.
U.S. Appl. No. 12/866,709, filed Aug. 17, 2010, Harold R. Bergen, III, Abandoned.
U.S. Appl. No. 14/777,236, filed Sep. 15, 2015, David R. Barnidge, Published.
U.S. Appl. No. 15/301,633, filed Oct. 3, 2016, David L. Murray, Issued.
U.S. Appl. No. 16/297,340, filed Mar. 8, 2019, David L. Murray, Allowed.
U.S. Appl. No. 15/329,512, filed Jan. 26, 2017, David R. Barnidge, Issued.
U.S. Appl. No. 16/646,279, filed Mar. 11, 2020, David L. Murray, Pending.
U.S. Appl. No. 16/646,289, filed Mar. 11, 2020, David L. Murray, Pending.
U.S. Appl. No. 16/331,228, filed Mar. 7, 2019, David R. Barnidge, Published.
U.S. Appl. No. 15/762,900, filed Mar. 23, 2018, David R. Barnidge, Published.
Lo et al., "Acid hydrolysis followed by matrix-assisted laser desorption/ionization mass spectrometry for the rapid diagnosis of serum protein biomarkers in patients with major depression," Rapid Commun. Mass Spectrometry, Jan. 22, 2009, 23(5):589-598.
Lo et al., "Rapid detection of alteration of serum IgG in patients with schizophrenia after risperidone treatment by matrix-assisted laser desorption ionization/time-of-flight mass spectrometry." Rapid Commun. Mass Spectrometry, Dec. 30, 2016, 30(24):2645-2649.
Botz et al., "Detecting monoclonal light chains in urine: micro LC-ESI-Q-TOF mass spectrometry compared to immunofixation electrophoresis," British journal of haematology, 167(3):437-8, Nov. 2014.
Dada et al., "High-Resolution Capillary Zone Electrophoresis with Mass Spectrometry Peptide Mapping of Therapeutic Proteins: Peptide Recovery and Post-translational Modification Analysis in Monoclonal Antibodies and Antibody-Drug Conjugates," Anal. Chem. 2017, vol. 89, pp. 11236-11242.
Haeney, M., "Monoclonal Immunoglobulins" in Immunoglobulins in Health and Disease. Immunology and Medicine Series, vol. 1, French M.A.H. (eds), Springer, Dordrecht 1986, 143-172.
Remily-Wood et al. Quantification of Peptides from Immunoglobulin Constant and Variable Regions by Liquid Chromatography-Multiple Reaction Monitoring Mass Spectrometry for Assessment of Multiple Myeloma Patients. Proteonnics Clin Appl. Oct. 2014; 8(0), pp. 783-795. (Year: 2014).
VanDuijn et al., "Quantitative measurement of immunoglobulins and free light chains using mass spectrometry," Analytical chemistry, 87(16):8268-74, Aug. 2015.
Ankeny et al., "B cells produce pathogenic antibodies and impair recovery after spinal cord injury in mice," Journal of Clinical Investigation, Oct. 2009, 119(10):2990-2999.
Attaelmannan et al., "Understanding and Identifying Monoclonal Gammopathies," Clinical Chemistry, 2000, 46(8B):1230-1238.
Bhattacharyya et al., "Biomarkers that discriminate multiple myeloma patients with or without skeletal involvement detected using SELDI-TOF mass spectrometry and statistical and machine learning tools," Disease Markers, 2006, 22:245-255.
Cumova et al., "Proteomic Analysis in Multiple Myeloma Research," Molecular Biotechnology, 2011, 47:83-93.
Fang et al., "Affinity separation and enrichment methods in proteomic analysis," Journal of Proteomics, 2008, 71:284-303.
Lu et al., "Development of Different Analysis Platforms with LC-MS for Pharmacokinetic Studies of Protein Drugs," Analytical Chemistry, Nov. 2009, 81(21):8715-8723.
Perdivara, "Structure Determination of Autoimmune Disease—Related Proteins by High Performance Liquid Chromatography—Mass Spectrometry," Dissertation for the degree of Doctor of Natural Sciences, University of Konstanz, 2009, 185 pages.
Siuti et al., "Decoding protein modifications using top-down mass spectrometry," Nature Methods, Oct. 2007, 4(10):817-821.
Tissot et al., "High-resolution two-dimensional protein electrophoresis of pathological plasma/serum," Applied and Theoretical Electrophoresis, 1991, 2:7-12.
Tsai et al., "Origin of the Isoelectric Heterogeneity of Monoclonal Immunoglobulin h1B4," Pharmaceutical Research, 1993, 10(11):1580-1586.
Hong et al., "A Method for Comprehensive Glycosite-Mapping and Direct Quantitation of Serum Glycoproteins," J. Proteome Res., Dec. 2015, 14(12):5179-5192.
ThermoFisher.com [online], "Protein Denaturing and Reducing Agents," available on or before Oct. 5, 2022, via Internet Archive: Wayback Machine URL<http://web.archive.org/web/20221005110723/https://www.thermofisher.com/us/en/home/life-science/protein-biology/protein-labeling-crosslinking/protein-modification/reducing-agents-protein-disulfides.html>, retrieved on Sep. 20, 2023, URL<https://www.thermofisher.com/us/en/home/life-science/protein-biology/protein-labeling-crosslinking/protein-modification/reducing-agents-protein-disulfides.html>, 3 pages.
Liu et al., "Assessment of antibody fragmentation by reversed-phase liquid chromatography and mass spectrometry," J. Chromatogr. B Analyt. Technol. Biomed. Life Sci., Dec. 2008, 876(1):13-23.
Torres et al., "The Immunoglobulin Heavy Chain Constant Region Affects Kinetic and Thermodynamic Parameters of Antibody Variable Region Interactions with Antigen, " J. Biol. Chem., May 2007, 282(18):13917-13927.
Nelson et al., "Detection of human IgM at m/z approximately 1 Mda," Rapid Commun. Mass Spectrom., 1995, 9(7):625.
Nelson et al., "Mass determination of human immunoglobulin IgM using matrix-assisted laser desorption/ionization time-of-flight mass spectrometry," Rapid Commun. Mass Spectrom., Aug. 1994, 8(8):627-631.
Janeway's Immunobiology, 8th ed., Murphy (ed)., 2011, p. 174, Fig. 5.15, 1 page.

* cited by examiner

GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI
SKAKGQPREP QVYTLPPSRD ELTKNQVSLT CLVKGFYPSD IAVEWESNGQ
PENNYKTTPP VLDSDGSFFL YSKLTVDKSR WQQGNVFSCS VMHEALHNHY
TQKSLSLSPG

FIG. 3A

PEVKFNWYVDGVEVHNAKTKPREEQYNSTYRVVSVLTVLHQDWLNG
KEYKCKVSNKALPAPIEKTISKAKGQPREPQVYTLPPSRDELTKNQV
SLTCLVKGFYPSDIAVEWESNGQPENNYKTTPPVLDSDGSFFLYSKLT
VDKSRWQQGNVFSCSVMHEALHNHYTQKSLSLSPG

FIG. 3B

GPSVFLFPPK PKDTLMISRT PEVTCVVVDV SHED / Aspartic acid cleavage site After acid hydrolysis

FIG. 3C

SEQUENCE LISTING

```
<160> NUMBER OF SEQ ID NOS: 7

<210> SEQ ID NO 1
<211> LENGTH: 210
<212> TYPE: PRT
<213> ORGANISM: Artificial
<220> FEATURE:
<223> OTHER INFORMATION: IdeS heavy chain acid cleavage product

<400> SEQUENCE: 1

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210


<210> SEQ ID NO 2
<211> LENGTH: 176
<212> TYPE: PRT
<213> ORGANISM: Artificial
<220> FEATURE:
<223> OTHER INFORMATION: IgG heavy chain acid hydrolysis product

<400> SEQUENCE: 2

Pro Glu Val Lys Phe Asn Trp Tyr Val Asp Gly Val Glu Val His Asn
1               5                   10                  15

Ala Lys Thr Lys Pro Arg Glu Glu Gln Tyr Asn Ser Thr Tyr Arg Val
            20                  25                  30

Val Ser Val Leu Thr Val Leu His Gln Asp Trp Leu Asn Gly Lys Glu
        35                  40                  45

Tyr Lys Cys Lys Val Ser Asn Lys Ala Leu Pro Ala Pro Ile Glu Lys
    50                  55                  60

Thr Ile Ser Lys Ala Lys Gly Gln Pro Arg Glu Pro Gln Val Tyr Thr
65                  70                  75                  80
```

```
Leu Pro Pro Ser Arg Asp Glu Leu Thr Lys Asn Gln Val Ser Leu Thr
                85                  90                  95

Cys Leu Val Lys Gly Phe Tyr Pro Ser Asp Ile Ala Val Glu Trp Glu
            100                 105                 110

Ser Asn Gly Gln Pro Glu Asn Asn Tyr Lys Thr Thr Pro Pro Val Leu
        115                 120                 125

Asp Ser Asp Gly Ser Phe Phe Leu Tyr Ser Lys Leu Thr Val Asp Lys
    130                 135                 140

Ser Arg Trp Gln Gln Gly Asn Val Phe Ser Cys Ser Val Met His Glu
145                 150                 155                 160

Ala Leu His Asn His Tyr Thr Gln Lys Ser Leu Ser Leu Ser Pro Gly
                165                 170                 175


<210> SEQ ID NO 3
<211> LENGTH: 34
<212> TYPE: PRT
<213> ORGANISM: Artificial
<220> FEATURE:
<223> OTHER INFORMATION: IgG heavy chain acid hydrolysis product

<400> SEQUENCE: 3

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp


<210> SEQ ID NO 4
<211> LENGTH: 10
<212> TYPE: PRT
<213> ORGANISM: Artificial
<220> FEATURE:
<223> OTHER INFORMATION: IgG heavy chain acid hydrolysis product
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Pro Glu Val Xaa Phe Xaa Trp Tyr Val Asp
1               5                   10


<210> SEQ ID NO 5
<211> LENGTH: 10
<212> TYPE: PRT
<213> ORGANISM: Artificial
<220> FEATURE:
<223> OTHER INFORMATION: IgG heavy chain acid hydrolysis product

<400> SEQUENCE: 5

Pro Glu Val Lys Phe Asn Trp Tyr Val Asp
1               5                   10


<210> SEQ ID NO 6
<211> LENGTH: 10
<212> TYPE: PRT
<213> ORGANISM: Artificial
<220> FEATURE:
<223> OTHER INFORMATION: IgG heavy chain acid hydrolysis product

<400> SEQUENCE: 6
```

-continued

```
Pro Glu Val Gln Phe Asn Trp Tyr Val Asp
1               5                   10


<210> SEQ ID NO 7
<211> LENGTH: 10
<212> TYPE: PRT
<213> ORGANISM: Artificial
<220> FEATURE:
<223> OTHER INFORMATION: IgG heavy chain acid hydrolysis product

<400> SEQUENCE: 7

Pro Glu Val Gln Phe Lys Trp Tyr Val Asp
1               5                   10
```

IDENTIFICATION AND MONITORING OF ACID HYDROLYSIS PRODUCTS OF IMMUNOGLOBULIN HEAVY CHAINS

CROSS-REFERENCE TO RELATED APPLICATIONS

This application is a National Stage application under 35 U.S.C. § 371 of International Application No. PCT/US2018/050846, having an International Filing Date of Sep. 13, 2018, which claims the benefit of U.S. Patent Application Ser. No. 62/558,056, filed on Sep. 13, 2017. The disclosure of the prior application is considered part of (and is incorporated by reference in) the disclosure of this application.

BACKGROUND

1. Technical Field

This document relates to materials and methods for identifying and/or quantifying immunoglobulin heavy chains (e.g., IgG heavy chains) in a sample, such as a biological sample, using mass spectrometry techniques. For example, IgG heavy chain acid hydrolysis products in a serum sample can be identified and/or quantified using mass spectrometry techniques without the need for any IgG cleavage reagents (e.g., enzymes).

2. Background Information

Human immunoglobulins contain two identical heavy chain polypeptides and two identical light chain polypeptides bound together by disulfide bonds. There are two different light chain isotypes (kappa and lambda) and five different heavy chain isotypes (IgG, IgA, IgM, IgD, and IgE).

SUMMARY

This document provides materials and methods for identifying and/or quantifying immunoglobulin heavy chains (e.g., IgG heavy chains) in a sample, such as a biological sample, using mass spectrometry (MS) techniques. In some cases, MS techniques can be used to identify and/or quantify IgG heavy chains in a serum sample in the absence of any IgG cleavage reagents (e.g., enzymes). As demonstrated herein, acid hydrolysis (e.g., with 5% acetic acid) can be used to disrupt antibody-immunoglobulin interactions and generate IgG immunoglobulin acid hydrolysis products. The accurate molecular mass of IgG heavy chain acid hydrolysis products coupled with top-down MS can be used to identify IgG heavy chains in patient serum. Typically, IgG is not cleaved by routine reagents (e.g., enzymes such as plasmin or trypsin), and thus IgG cleavage requires highly specific cleaving enzymes. This methodology holds promise as a sensitive and specific diagnostic tool to aid in monitoring a patient's immune system that, without the need for IgG cleavage reagents (e.g., enzymes), can reduce costs and/or save time.

In general, one aspect of this document features a method for identifying IgG heavy chain acid hydrolysis products in a sample. The method includes, or consists essentially of, providing a sample comprising immunoglobulins, immunopurifying IgG immunoglobulins from the sample, subjecting the IgG immunoglobulins to an acid to hydrolyze the IgG immunoglobulins, subjecting the hydrolyzed IgG immunoglobulins to a MS technique to obtain a mass spectrum of the sample, and identifying the presence of IgG heavy chain acid hydrolysis products based on the multiply charged ion peaks in the spectrum. The IgG heavy chain acid hydrolysis product can include the amino acid sequence PEVXFXWYVD (SEQ ID NO:4). The amino acid sequence PEVXFXWYVD (SEQ ID NO:4) can be at the N-terminus of the IgG heavy chain acid hydrolysis product. The IgG immunoglobulins can include IgG1 IgG immunoglobulins, and the IgG1 heavy chain acid hydrolysis products can include the amino acid sequence PEVKFNWYVD (SEQ ID NO:5). The IgG immunoglobulins can include IgG2 IgG immunoglobulins and/or IgG4 immunoglobulins, and the IgG2 and/or IgG4 heavy chain acid hydrolysis products can include the amino acid sequence PEVQFNWYVD (SEQ ID NO:6). The IgG immunoglobulins can include IgG3 IgG immunoglobulins, and the IgG3 heavy chain acid hydrolysis products can include the amino acid sequence PEVQFKWYVD (SEQ ID NO:7). The IgG heavy chain acid hydrolysis product can be glycosylated. The sample can be a biological fluid (e.g., blood, serum, plasma, urine, lachrymal fluid, or saliva). The biological fluid can be serum. The immunopurifying can include using an anti-human IgG kappa antibody. The anti-human IgG kappa antibody can be a non-human antibody (e.g., a camelid antibody, a cartilaginous fish antibody, llama, sheep, goat, rabbit, or a mouse antibody). The non-human antibody can be a camelid antibody. The anti-human IgG kappa antibody can be a single domain antibody fragment. The acid can be acetic acid (e.g., 5% acetic acid). The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The MS technique can be a top-down MS technique. The immunoglobulins can be intact (e.g., not fragmented) during the MS technique. The method also can include contacting the sample with a reducing agent prior to subjecting the sample to the MS technique. The reducing agent can be tris(2-carboxyethyl)phosphine (TCEP).

In another aspect, this document features a method for quantifying IgG heavy chain acid hydrolysis products in a sample. The method includes, or consists essentially of, providing a sample comprising immunoglobulins, immunopurifying IgG immunoglobulins from the sample, subjecting the IgG immunoglobulins to an acid to hydrolyze the IgG immunoglobulins, subjecting the hydrolyzed IgG immunoglobulins to a MS technique to obtain a mass spectrum of the sample, identifying the presence of IgG heavy chain acid hydrolysis products based on the multiply charged ion peaks in the spectrum, and converting the peak area of the identified peaks to a molecular mass to quantify the IgG heavy chain acid hydrolysis products in the sample. The IgG heavy chain acid hydrolysis product can include the amino acid sequence PEVXFXWYVD (SEQ ID NO:4). The amino acid sequence PEVXFXWYVD (SEQ ID NO:4) can be at the N-terminus of the IgG heavy chain acid hydrolysis product. The IgG immunoglobulins can include IgG1 IgG immunoglobulins, and the IgG1 heavy chain acid hydrolysis products can include the amino acid sequence PEVKFNWYVD (SEQ ID NO:5). The IgG immunoglobulins can include IgG2 IgG immunoglobulins and/or IgG4 immunoglobulins, and the IgG2 and/or IgG4 heavy chain acid hydrolysis products can include the amino acid sequence PEVQFNWYVD (SEQ ID NO:6). The IgG immunoglobulins can include IgG3 IgG immunoglobulins, and the IgG3 heavy chain acid hydrolysis products can include the amino acid sequence PEVQFKWYVD (SEQ ID NO:7).

The IgG heavy chain acid hydrolysis product can be glycosylated. The sample can be a biological fluid (e.g., blood, serum, plasma, urine, lachrymal fluid, or saliva). The biological fluid can be serum. The immunopurifying can include using an anti-human IgG kappa antibody. The anti-human IgG kappa antibody can be a non-human antibody (e.g., a camelid antibody, a cartilaginous fish antibody, llama, sheep, goat, rabbit, or a mouse antibody). The non-human antibody can be a camelid antibody. The anti-human IgG kappa antibody can be a single domain antibody fragment. The acid can be acetic acid (e.g., 5% acetic acid). The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The MS technique can be a top-down MS technique. The immunoglobulins can be intact (e.g., not fragmented) during the MS technique. The method also can include contacting the sample with a reducing agent prior to subjecting the sample to the MS technique. The reducing agent can be TCEP.

In another aspect, this document features a method for diagnosing a disorder in a patient, where the disorder can be associated with altered production of IgG immunoglobulins. The method includes, or consists essentially of, providing a sample comprising immunoglobulins, immunopurifying IgG immunoglobulins from the sample, subjecting the IgG immunoglobulins to an acid to hydrolyze the IgG immunoglobulins, subjecting the hydrolyzed IgG immunoglobulins to a MS technique to obtain a mass spectrum of the sample, identifying the presence of IgG heavy chain acid hydrolysis products based on the multiply charged ion peaks in the spectrum, converting the peak area of the identified peaks to a molecular mass to quantify the IgG heavy chain acid hydrolysis products in the sample, comparing the quantity of IgG heavy chain acid hydrolysis products to a reference value, and identifying the patient as having a disorder associated with altered production of IgG immunoglobulin when the quantity of IgG heavy chain acid hydrolysis products in the sample is increased or decreased relative to the reference value. The disorder can include increased production of IgG immunoglobulins (e.g., multiple myeloma, primary systemic amyloidosis, monoclonal gammopathy of undetermined significance, hepatitis, liver cirrhosis, and connective tissue disease). The patient can be a mammal (e.g., a human). The IgG heavy chain acid hydrolysis product can include the amino acid sequence PEVXFXWYVD (SEQ ID NO:4). The amino acid sequence PEVXFXWYVD (SEQ ID NO:4) can be at the N-terminus of the IgG heavy chain acid hydrolysis product. The IgG immunoglobulins can include IgG1 IgG immunoglobulins, and the IgG1 heavy chain acid hydrolysis products can include the amino acid sequence PEVKFNWYVD (SEQ ID NO:5). The IgG immunoglobulins can include IgG2 IgG immunoglobulins and/or IgG4 immunoglobulins, and the IgG2 and/or IgG4 heavy chain acid hydrolysis products can include the amino acid sequence PEVQFNWYVD (SEQ ID NO:6). The IgG immunoglobulins can include IgG3 IgG immunoglobulins, and the IgG3 heavy chain acid hydrolysis products can include the amino acid sequence PEVQFKWYVD (SEQ ID NO:7). The IgG heavy chain acid hydrolysis product can be glycosylated. The sample can be a biological fluid (e.g., blood, serum, plasma, urine, lachrymal fluid, or saliva). The biological fluid can be serum. The immunopurifying can include using an anti-human IgG kappa antibody. The anti-human IgG kappa antibody can be a non-human antibody (e.g., a camelid antibody, a cartilaginous fish antibody, llama, sheep, goat, rabbit, or a mouse antibody). The non-human antibody can be a camelid antibody. The anti-human IgG kappa antibody can be a single domain antibody fragment. The acid can be acetic acid (e.g., 5% acetic acid). The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The MS technique can be a top-down MS technique. The immunoglobulins can be intact (e.g., not fragmented) during the MS technique. The method also can include contacting the sample with a reducing agent prior to subjecting the sample to the MS technique. The reducing agent can be TCEP.

In another aspect, this document features a method for treating a disorder in a patient, where the disorder can be associated with altered production of IgG immunoglobulins. The method includes, or consists essentially of, identifying said patient as having the disorder by providing a sample comprising immunoglobulins, immunopurifying IgG immunoglobulins from the sample, subjecting the IgG immunoglobulins to an acid to hydrolyze the IgG immunoglobulins, subjecting the hydrolyzed IgG immunoglobulins to a MS technique to obtain a mass spectrum of the sample, identifying the presence of IgG heavy chain acid hydrolysis products based on the multiply charged ion peaks in the spectrum, converting the peak area of the identified peaks to a molecular mass to quantify the IgG heavy chain acid hydrolysis products in the sample, comparing the quantity of IgG heavy chain acid hydrolysis products to a reference value, and identifying the patient as having a disorder associated with altered production of IgG immunoglobulin when the quantity of IgG heavy chain acid hydrolysis products in the sample is increased or decreased relative to the reference value; and administering to said patient a therapeutic agent to treat said disorder. The method also can include performing a plasma exchange or a stem cell transplant on said patient. The disorder can include increased production of IgG immunoglobulins (e.g., multiple myeloma, primary systemic amyloidosis, monoclonal gammopathy of undetermined significance, hepatitis, liver cirrhosis, and connective tissue disease). The patient can be a mammal (e.g., a human). The IgG heavy chain acid hydrolysis product can include the amino acid sequence PEVXFXWYVD (SEQ ID NO:4). The amino acid sequence PEVXFXWYVD (SEQ ID NO:4) can be at the N-terminus of the IgG heavy chain acid hydrolysis product. The IgG immunoglobulins can include IgG1 IgG immunoglobulins, and the IgG1 heavy chain acid hydrolysis products can include the amino acid sequence PEVKFNWYVD (SEQ ID NO:5). The IgG immunoglobulins can include IgG2 IgG immunoglobulins and/or IgG4 immunoglobulins, and the IgG2 and/or IgG4 heavy chain acid hydrolysis products can include the amino acid sequence PEVQFNWYVD (SEQ ID NO:6). The IgG immunoglobulins can include IgG3 IgG immunoglobulins, and the IgG3 heavy chain acid hydrolysis products can include the amino acid sequence PEVQFKWYVD (SEQ ID NO:7). The IgG heavy chain acid hydrolysis product can be glycosylated. The sample can be a biological fluid (e.g., blood, serum, plasma, urine, lachrymal fluid, or saliva). The biological fluid can be serum. The immunopurifying can include using an anti-human IgG kappa antibody. The anti-human IgG kappa antibody can be a non-human antibody (e.g., a camelid antibody, a cartilaginous fish antibody, llama, sheep, goat, rabbit, or a mouse antibody). The non-human antibody can be a camelid antibody. The anti-human IgG kappa antibody can be a single domain antibody fragment. The acid can be acetic acid (e.g., 5% acetic acid). The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The MS technique can be a top-down MS technique. The immunoglobulins can be intact (e.g., not fragmented) during the MS technique. The method also can include contacting the sample with a reducing agent prior to subjecting the sample to the MS technique. The reducing agent can be TCEP.

In another aspect, this document features a method of monitoring a treatment of a disorder in a patient, where the disorder can be associated with altered production of IgG immunoglobulins. The method includes, or consists essentially of, providing an initial sample including immunoglobulins from the patient where the initial sample can be obtained from the patient prior to the treatment, providing one or more secondary samples including immunoglobulins where the one or more secondary samples can be obtained from the patient (e.g., during the treatment, after the treatment, or both), immunopurifying IgG immunoglobulins from the samples, subjecting the IgG immunoglobulins to an acid to hydrolyze the IgG immunoglobulins, subjecting the hydrolyzed IgG immunoglobulins to a MS technique to obtain a mass spectrum of the samples, identifying the presence of IgG heavy chain acid hydrolysis products in said samples based on the multiply charged ion peaks in the spectrum, converting the peak area of the identified peaks to a molecular mass to quantify the IgG heavy chain acid hydrolysis products in the samples, and comparing the quantity of the IgG heavy chain acid hydrolysis products from the initial sample and the one or more secondary samples. The disorder can include increased production of IgG immunoglobulins (e.g., multiple myeloma, primary systemic amyloidosis, monoclonal gammopathy of undetermined significance, hepatitis, liver cirrhosis, and connective tissue disease). The patient can be a mammal (e.g., a human). The IgG heavy chain acid hydrolysis product can include the amino acid sequence PEVXFXWYVD (SEQ ID NO:4). The amino acid sequence PEVXFXWYVD (SEQ ID NO:4) can be at the N-terminus of the IgG heavy chain acid hydrolysis product. The IgG immunoglobulins can include IgG1 IgG immunoglobulins, and the IgG1 heavy chain acid hydrolysis products can include the amino acid sequence PEVKFNWYVD (SEQ ID NO:5). The IgG immunoglobulins can include IgG2 IgG immunoglobulins and/or IgG4 immunoglobulins, and the IgG2 and/or IgG4 heavy chain acid hydrolysis products can include the amino acid sequence PEVQFNWYVD (SEQ ID NO:6). The IgG immunoglobulins can include IgG3 IgG immunoglobulins, and the IgG3 heavy chain acid hydrolysis products can include the amino acid sequence PEVQFKWYVD (SEQ ID NO:7). The IgG heavy chain acid hydrolysis product can be glycosylated. The sample can be a biological fluid (e.g., blood, serum, plasma, urine, lachrymal fluid, or saliva). The biological fluid can be serum. The immunopurifying can include using an anti-human IgG kappa antibody. The anti-human IgG kappa antibody can be a non-human antibody (e.g., a camelid antibody, a cartilaginous fish antibody, llama, sheep, goat, rabbit, or a mouse antibody). The non-human antibody can be a camelid antibody. The anti-human IgG kappa antibody can be a single domain antibody fragment. The acid can be acetic acid (e.g., 5% acetic acid). The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The MS technique can be a top-down MS technique. The immunoglobulins can be intact (e.g., not fragmented) during the MS technique. The method also can include contacting the sample with a reducing agent prior to subjecting the sample to the MS technique. The reducing agent can be TCEP.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 3A-3C show IgG cleavage fragments. A) An IgG subclass 1 constant region amino acid sequence (SEQ ID NO:1) after cleavage with the IdeS enzyme. Residue D270 is highlighted. B) IgG subclass 1 constant region amino acid sequence (SEQ ID NO:2) after acid hydrolysis. C) A peptide fragment (SEQ ID NO:3) produced from the acid hydrolysis of an IgG IdeS cleavage product (shown in FIG. 3A).

DETAILED DESCRIPTION

Figure 1A:
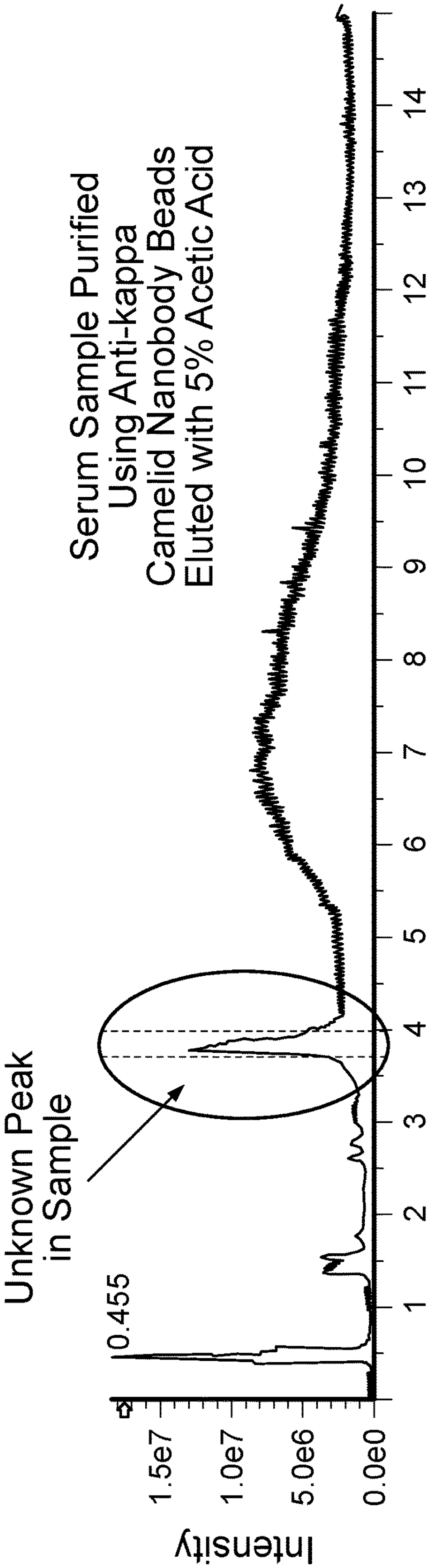
FIGS. 1A-1C contain MS spectra of IgG in normal pooled serum. A) A total ion chromatogram (TIC) of IgM purified from serum with an unknown peak at about 4 minutes. B) A summed mass spectrum of the unknown peak in FIG. 1A. C) A deconvoluted mass spectrum of the peaks in FIG. 1B showing molecular masses that give a pattern similar to those observed by cleaving IgG using IdeS.

IgG immunoglobulins are the main type of antibody found in blood and extracellular fluid, and are important for protecting the body from infection. For example, IgG can control infections by, for example, binding pathogens (e.g., viruses, bacteria, and fungi) to allow their recognition and ingestion by phagocytic immune cells, activating the complement system, and/or binding and neutralizing toxins. IgG immunoglobulins are also the only isotype that can pass through the human placenta, thereby providing protection to the fetus in utero. IgG immunoglobulins in serum are typically monitored by cleaving the IgG immunoglobulins with exogenous enzymes, and detecting the cleavage fragments using low resolution gel electrophoresis.

This document provides materials and methods for identifying and/or quantifying immunoglobulins (e.g., IgG immunoglobulins) in a sample, such as a biological sample, using MS techniques. For example, identifying and/or quantifying immunoglobulin heavy chains (e.g., IgG heavy chains) in a sample can be used to identify and/or quantify the immunoglobulin (e.g., IgG immunoglobulin) in a sample. In some cases, the identification and/or quantification of IgG heavy chain acid hydrolysis products can be used to identify and/or quantify IgG heavy chains and thus IgG immunoglobulins (e.g., therapeutic IgG monoclonal antibodies (mAbs)). The immunoglobulins (e.g., IgG immunoglobulins) can be from any appropriate immunoglobulin subclass. For example, an IgG immunoglobulin can be an IgG subclass 1 (IgG1), IgG subclass 2 (IgG2), IgG subclass 3 (IgG3), or IgG subclass 4 (IgG4) IgG immunoglobulin.

In some cases, MS techniques can be used to identify and/or quantify heavy chains (e.g., IgG heavy chains) in a serum sample without the need for any heavy chain cleavage reagents (e.g., enzymes). Examples of IgG heavy chain cleavage reagents include, without limitation, IgG cleavage enzymes (e.g., immunoglobulin-degrading enzymes from *Streptococcus* (IdeS), immunoglobulin-degrading enzymes from *Streptococcus equi* subspecies *zooepidemicus* (IdeZ), and papain). For example, in some cases, the MS techniques described herein can be used to identify and/or quantify IgG heavy chains without the need for an IdeS enzyme.

As described herein, IgG heavy chain acid hydrolysis products can be detected in IgG-purified samples using MS. Also described herein is the accurate molecular mass of IgG heavy chain acid hydrolysis products. Because the accurate molecular mass of IgG heavy chain acid hydrolysis products is easily identified by MS, and multiple different IgG heavy chain acid hydrolysis products (e.g., non-glycosylated hydrolysis products and glycosylated hydrolysis products) can be identified in the same analysis. In some cases, a method described herein can include the use of a liquid chromatography MS (LC-MS). For example, IgG immunoglobulin acid hydrolysis products can be identified by molecular mass using LC-MS. In some cases, electrospray ionization MS (ESI-MS) techniques can be used, for example, an electrospray ionization quadrupole time-of-flight (ESI-Q-TOF) MS technique. In some cases, a MS technique can be a top-down MS technique. The use of mass over charge (m/z), optionally with additional techniques, such as gel electrophoresis and/or peptide sequencing, provides a more direct assessment of IgG heavy chain acid hydrolysis products because it can be used to determine the quantity of the IgG heavy chain acid hydrolysis products. Heavy chain acid hydrolysis products (e.g., IgG heavy chain acid hydrolysis products) can be from an immunoglobulin of any appropriate immunoglobulin subclass. For example, an IgG heavy chain acid hydrolysis product can an IgG1, IgG2, IgG3, or IgG4 heavy chain acid hydrolysis product.

Heavy chain acid hydrolysis products (e.g., IgG heavy chain acid hydrolysis products) can be generated by cleavage at any appropriate location. In some cases, heavy chain acid hydrolysis products can be generated by cleavage of the amino acid backbone. In some cases, heavy chain acid hydrolysis products can be generated without acid reduction of disulfide (i.e., disulphide) bonds (e.g., without acid reduction of disulfide bonds between heavy and light chains and/or without acid reduction of disulfide bonds between heavy-heavy chain disulfide linkages). For example, heavy chain acid hydrolysis products can maintain the presence of disulfide bonds (e.g., disulfide bonds between heavy and light chains and/or without acid reduction of disulfide bonds between heavy-heavy chain disulfide linkages).

Heavy chain acid hydrolysis products (e.g., IgG heavy chain acid hydrolysis products) can be generated by any appropriate acid. Examples of acids that can be used to generate IgG heavy chain acid hydrolysis products include, without limitation, acetic acid. In some cases, the acid can be acetic acid. An acid used to generate IgG heavy chain acid hydrolysis products can be any appropriate concentration of acid. For example, acetic acid can be from about 2% to about 15% (e.g., about 2% to about 12%, about 2% to about 10%, about 2% to about 8%, about 2% to about 5%, about 3% to about 15%, about 5% to about 15%, about 8% to about 15%, about 10% to about 15%, about 12% to about 15%, about 3% to about 12%, or about 4% to about 10%). In some cases, when acetic acid is used to generate IgG heavy chain acid hydrolysis products, the acetic acid can be about 5% acetic acid. In some cases, an acid can hydrolyze (e.g., cleave) an IgG heavy chain at amino acid residue D270.

Figure 5A:
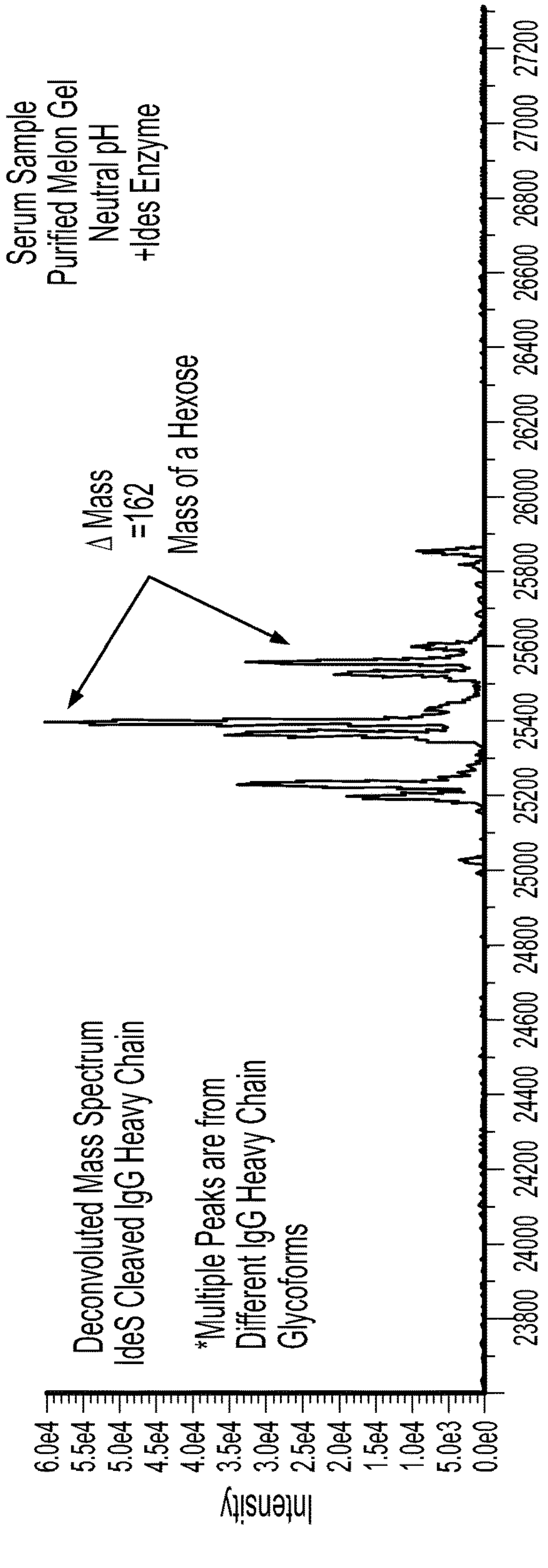
FIGS. 5A-5B contain MS spectra showing that the mass differences of the IgG heavy glycoforms produced by cleavage with the IdeS enzyme match those obtained by acid hydrolysis. A) A deconvoluted mass spectrum of IgG heavy chain fragment glycoforms produced by cleavage with IdeS. B) A deconvoluted mass spectrum of IgG heavy chain acid hydrolysis products. The difference in molecular mass between the glycoforms in 5A vs. 5B is equal to the molecular mass of the peptide fragment in FIG. 3C.
Figure 5B:
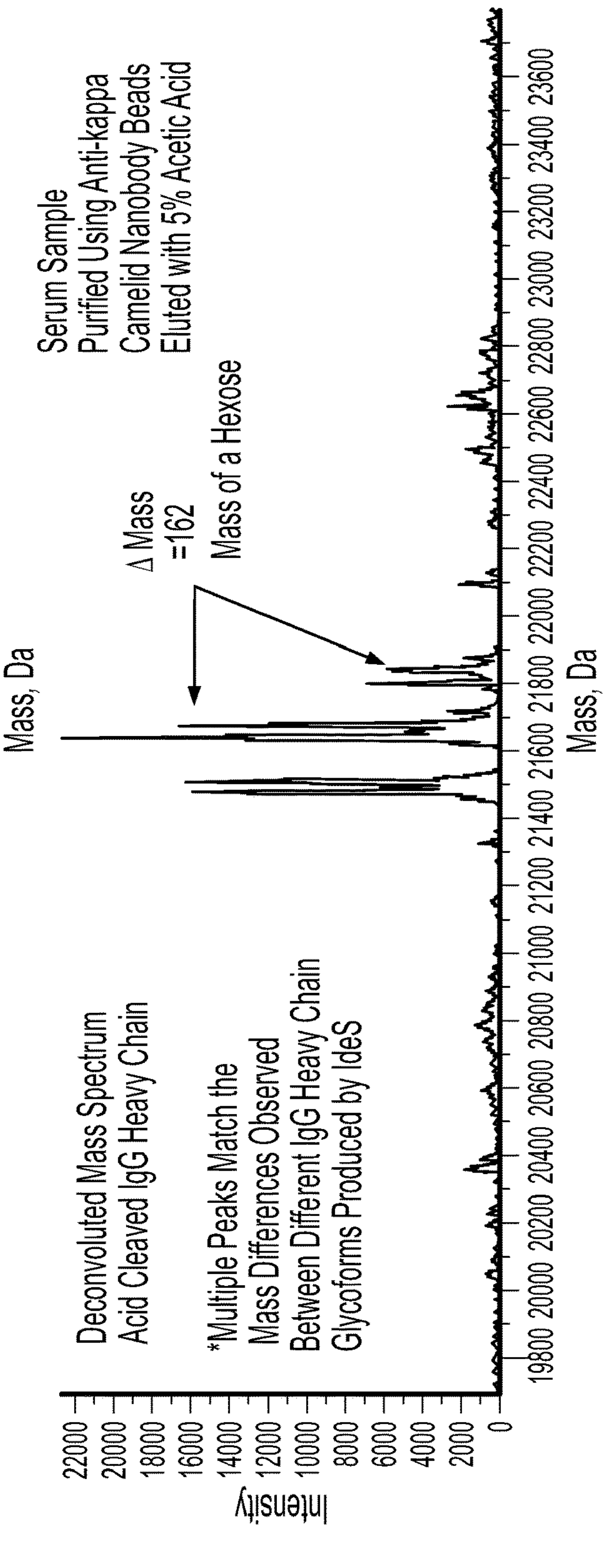

In some cases, heavy chain acid hydrolysis products (e.g., IgG heavy chain acid hydrolysis products) can be identified by molecular mass. The molecular mass(es) for IgG heavy chain acid hydrolysis products can be as shown in FIG. 5B. For example, an IgG heavy chain acid hydrolysis product (e.g., a non-glycosylated IgG heavy chain acid hydrolysis product) can have a molecular mass of about 21,600 Da to about 21,700 Da (e.g., 21,673.8 Da). For example, an IgG heavy chain acid hydrolysis product (e.g., a glycosylated IgG heavy chain acid hydrolysis product) can have a molecular mass of about 21,750 Da to about 21,850 Da (e.g., 21,803.4 Da).

In some cases, heavy chain acid hydrolysis products (e.g., IgG heavy chain acid hydrolysis products) can be identified by amino acid sequence. An IgG heavy chain acid hydrolysis product can include the amino acid sequence PEVXFXWYVD (SEQ ID NO:4), where the X at residue 4 can be a lysine (K) or a glutamine (Q), and where the X at residue 6 can be an asparagine (N) or a K. Examples of IgG heavy chain acid hydrolysis product amino acid sequences include, without limitation, PEVKFNWYVD (SEQ ID NO:5), PEVQFNWYVD (SEQ ID NO:6) and PEVQFKWYVD (SEQ ID NO:7). For example, an IgG1 heavy chain acid hydrolysis product can include the amino acid sequence PEVKFNWYVD (SEQ ID NO:5) at its N-terminus. For example, an IgG2 heavy chain acid hydrolysis product can include the amino acid sequence PEVQFNWYVD (SEQ ID NO:6) at its N-terminus. For example, an IgG4 heavy chain acid hydrolysis product can include the amino acid sequence PEVQFNWYVD (SEQ ID NO:6) at its N-terminus. For example, an IgG3 heavy chain acid hydrolysis product can include the amino acid sequence PEVQFKWYVD (SEQ ID NO:7) at its N-terminus.

In some cases, a heavy chain acid hydrolysis product (e.g., an IgG heavy chain acid hydrolysis product) can include a posttranslational modification (e.g., glycosylation). For example, a glycosylated IgG heavy chain acid hydrolysis product can include any appropriate carbohydrate (e.g., a hexose).

The methods described herein, also referred to as monoclonal immunoglobulin Rapid Accurate Mass Measurement (miRAMM), can be coupled with immunopurification (e.g., IgG immunopurification) to identify and/or quantify heavy chain acid hydrolysis products (e.g., IgG heavy chain acid hydrolysis products) in a sample (e.g., a serum sample) without the need for additional instrumentation or any IgG cleavage reagents (e.g., enzymes). The materials and methods described herein can be used to screen biological samples for the presence or absence, quantity, and/or glycoform of IgG heavy chain acid hydrolysis products. In some cases, the identifying and/or quantifying IgG heavy chain acid hydrolysis products can be used for identifying a disease or disorder characterized by altered (e.g., increased or decreased) IgG immunoglobulin levels in a patient, for monitoring IgG immunoglobulin levels (e.g., therapeutic IgG mAb levels) in a patient, and/or for monitoring treatment of a disease or disorder characterized by altered IgG immunoglobulin levels. The speed, sensitivity, resolution, and robustness of MS make the present methods superior than gel electrophoresis for screening samples for presence or absence, quantity, and/or glycoform(s) of IgG heavy chain acid hydrolysis products.

Samples and Sample Preparation

The materials and methods for identifying and quantifying heavy chain acid hydrolysis products (e.g., IgG heavy chain acid hydrolysis products) as described herein can include any appropriate sample. A sample can be any biological sample, such as a tissue (e.g., adipose, liver, kidney, heart, muscle, bone, or skin tissue) or biological fluid (e.g., blood, serum, plasma, urine, lachrymal fluid, or saliva). The sample can be from a patient that has immunoglobulins, which includes but is not limited to a mammal, e.g. a human, dog, cat, primate, rodent, pig, sheep, cow, horse, bird, reptile, or fish. A sample can also be a man-made reagent, such as a mixture of known composition or a control sample. In some cases, the sample is serum from a human patient.

A sample can be treated to remove components that could interfere with the MS technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be deproteinized. For example, a plasma sample can have serum proteins precipitated using conventional reagents such as acetonitrile, KOH, NaOH, or others known to those having ordinary skill in the art, optionally followed by centrifugation of the sample.

Immunoglobulins (e.g., immunoglobulins and polypeptides bound to the immunoglobulins) can be isolated from the samples or enriched (i.e. concentrated) in a sample using standard methods known in the art. Such methods include removing one or more non-immunoglobulin contaminants from a sample. In some cases, the samples can be enriched or purified using immunopurification, centrifugation, filtration, ultrafiltration, dialysis, ion exchange chromatography, size exclusion chromatography, protein A/G affinity chromatography, affinity purification, precipitation, gel electrophoresis, capillary electrophoresis, chemical fractionation (e.g., antibody purification kits, such as Melon Gel Purification), and aptamer techniques. For example, the immunoglobulins can be purified by chemical-based fractionation, e.g., Melon Gel Chromatography (Thermo Scientific), where Melon Gel resins bind to non-immunoglobulin proteins in a sample and allow immunoglobulins to be collected in the flow-through fraction; or by affinity purification, e.g., by Protein G purification, where immunoglobulins are bound by those proteins at physiologic pH and then released from the proteins by lowering the pH. When serum, plasma, or whole blood samples are used, a sample, such as a 10-250 μl sample (e.g., a 50 μl sample), can be directly subjected to purification (e.g., immunopurification). Size exclusion principles such as a TurboFlow column can also be employed to separate the non-immunoglobulin contaminants from a sample. When urine samples are used, a urine sample can be buffered, e.g., a 50 μl urine sample can be diluted first with 50 μl of 50 mM ammonium bicarbonate.

A sample can be subjected to immunopurification prior to analysis by MS. In some cases, the sample can be immunoglobulin enriched. Immunopurification can result in enrichment of one or more immunoglobulins (e.g., IgG immunoglobulins). Purified immunoglobulins can be polyclonal, monoclonal, or oligoclonal. For example, immunopurification can separate or enrich IgG immunoglobulins in a sample. Immunopurification can involve contacting a sample containing the desired antigen with an affinity matrix including an antibody (e.g. single domain antibody fragments, also referred to as nanobodies) to the antigen covalently attached to a solid phase (e.g., beads such as agarose beads). Antigens in the sample become bound to the affinity matrix through an immunochemical bond. The affinity matrix is then washed to remove any unbound species. The antigen is then removed from the affinity matrix by altering the chemical composition of a solution in contact with the affinity matrix. The immunopurification may be conducted on a column containing the affinity matrix, in which case the solution is an eluent or in a batch process, in which case the affinity matrix is maintained as a suspension in the solution. In some cases, the antibody can be a labelled antibody (e.g. a biotinylated antibody) and a binding partner of the label (e.g., avidin and/or streptavidin) can be attached to the solid phase.

In some embodiments, single domain antibody fragments (SDAFs) with an affinity for immunoglobulins can be used in the immunopurification process. SDAFs can be derived from heavy chain antibodies of non-human sources (e.g., camelids, fish, llama, sheep, goat, rabbit, or mouse), heavy chain antibodies of human sources, and light chain antibodies of humans. SDAFs possess unique characteristics, such as low molecular weight, high physical-chemical stability, good water solubility, and the ability to bind antigens inaccessible to conventional antibodies. For example, IgG immunoglobulins can be immunopurified using anti-IgG (e.g., anti-IgG kappa) camelid nanobodies.

In some embodiments, isolation of immunoglobulins can be performed with an entity other than a traditional antibody—which contains both heavy and light chains (such as those used in immunofixation electrophoresis (IFE) and various known clinical immunoassays). Traditional antibodies contain heavy and/or light chains with masses that may overlap with the masses of the immunoglobulins in the sample of interest (e.g., human immunoglobulins). Therefore, these antibodies may interfere in the mass spectra of the patient's immunoglobulins. SDAFs may have masses ranging from 12,500-15,000 Da and, using the methods described herein, may carry a single charge thus generating a signal in the range of 12,500-15,000 m/z, which does not overlap with the signals generated by human heavy chains or light chains. The identification of human light chains and heavy chains by molecular mass can be done as described elsewhere (see, e.g., WO 2015/154052). Thus, in some embodiments, the use of specific isolation of IgG immunoglobulins (e.g., immunoglobulins and polypeptides bound to the immunoglobulins) utilizing SDAFs, coupled with mass identification, results in a specific and sensitive method for the detection of heavy chain acid hydrolysis products (e.g., IgG heavy chain acid hydrolysis products).

In some cases, the immunoglobulins (e.g., IgG immunoglobulins) are substantially isolated. By "substantially isolated" is meant that the immunoglobulins are at least partially or substantially separated from the sample from which they were provided. Partial separation can include, for example, a sample enriched in the immunoglobulins. Substantial separation can include samples containing at least about 10%, at least about 20%, at least about 30%, at least about 40%, at least about 50%, at least about 60%, at least about 70%, at least about 80%, at least about 90%, at least about 95%, at least about 97%, or at least about 99% by weight of the immunoglobulin.

In some cases, intact immunoglobulins (e.g., not fragmented) can be further processed to decouple the light chains in a total immunoglobulin sample from the heavy chain immunoglobulins. Decoupling can be achieved by treating the total immunoglobulins with a reducing agent, such as DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP, 2-mercapto-ethanol, and salt forms thereof. In some cases, the reducing step is performed at elevated temperature, e.g., in a range from about 30° C. to about 65° C., such as about 55° C., in order to denature the proteins. In some cases, the sample is further treated, e.g., by modifying the pH of the sample or buffering the sample. In some cases, the sample can be acidified. In some cases, the sample can be neutralized (e.g., by the addition of a base such as bicarbonate).

In some cases, the antigen binding fragments (Fab) of immunoglobulins can be cleaved from the intact immunoglobulins using proteases such as pepsin. Excess reagents and salts can be removed from the samples using methods known to those having ordinary skill in the art.

Mass Spectrometry Methods

The materials and methods for identifying and quantifying heavy chain acid hydrolysis products (e.g., IgG heavy chain acid hydrolysis products) as described herein can include any appropriate MS technique. After sample preparation, a sample can be subjected to a MS technique, either directly or after separation on a high performance liquid chromatography column (HPLC). In some cases, LC-MS can be used to analyze the mass spectrum of the ions. For example, the method can be used to identify multiply charged ions (e.g., the +1 ions, +2 ions, +3 ions, +4 ions, +5 ions, +6 ions, +7 ions, +8 ions, +9 ions, +10 ions, +11 ions, +12 ions, +13 ions, +14 ions, +15 ions, +16 ions, +17 ions, +18 ions, +19 ions, +20 ions, +21 ions, +22 ions, +23 ions, +24 ions, +25 ions, and +26 ions), resulting from the heavy chain acid hydrolysis products (e.g., IgG heavy chain acid hydrolysis products) in the sample. In some cases, the samples are not fragmented during the MS technique. LC-MS is an analytical technique that combines the physical separation capabilities of liquid chromatography with the mass analysis capabilities of MS, and is suitable for detection and potential identification of chemicals in a complex mixture. Any LC-MS instrument can be used, e.g., the ABSciex 5600 Mass Spectrometer. In some cases, microflowLC-MS can be utilized. Any suitable microflow instrument can be used, e.g., the Eksigent Ekspert 200 microLC. The ion mass spectrum can be analyzed for one or more peaks corresponding to one or more heavy chain acid hydrolysis products (e.g., IgG heavy chain acid hydrolysis products) in the sample. For example, one or more ion peaks, e.g., a +25 ion peak, can be examined to identify and monitor the IgG heavy chain acid hydrolysis products in the sample.

In some cases, ESI-Q-TOF MS can be used to analyze the mass spectrum of a sample, e.g., the mass spectrum of the +25 charge state of the heavy chain acid hydrolysis products (e.g., IgG heavy chain acid hydrolysis products) in the sample. ESI MS is a useful technique for producing ions from macromolecules because it overcomes the propensity of these molecules to fragment when ionized. In addition, ESI often produces multiply charged ions, effectively extending the mass range of the analyzer to accommodate the orders of magnitude observed in proteins and other biological molecules. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). The time-of-flight (TOF) analyzer uses an electric field to accelerate the ions through the same potential, and then measures the time they take to reach the detector. If the particles all have the same charge, the kinetic energies are identical, and their velocities depend only on their masses. Lighter ions reach the detector first. Any ESI-Q-TOF mass spectrometer can be used, e.g., the ABSciex TripleTOF 5600 quadrupole TOF mass spectrometer. The mass spectrum, e.g., the mass spectrum of multiply charged heavy chain acid hydrolysis product (e.g., the IgG heavy chain acid hydrolysis product) ions, can be analyzed to identify one or more peaks at an appropriate mass/charge expected for the heavy chain acid hydrolysis products. For example, for the IgG heavy chain acid hydrolysis products, the peaks (e.g., fragment ion peaks) can occur at about 100-1000 m/z. In some cases, the peaks can occur at about 150-750 m/z (e.g., about 225-600 m/z for the +25 ion).

The multiply charged ion peaks can be converted to a molecular mass using known techniques. For example, multiply charged ion peak centroids can be used to calculate average molecular mass and the peak area value used for quantification is supplied by a software package. Specifically, multiple ion deconvolution can be performed using the Bayesian Protein Reconstruct software package in the BioAnalyst companion software package in ABSCIEX Analyst TF 1.6. Deconvoluted and multiply charged ions can also be manually integrated using the Manual Integration 33 script in Analyst TF. Providing the molecular mass for the heavy chain acid hydrolysis products (e.g., IgG heavy chain acid hydrolysis products) in the sample facilitates sequencing and identification of the heavy chain acid hydrolysis products (e.g., IgG heavy chain acid hydrolysis products) in the sample. For example, for the IgG heavy chain acid hydrolysis products, the molecular mass can be from about 21,000 Da to about 22,000 Da. In some cases, the molecular mass of an IgG heavy chain acid hydrolysis product (e.g., a non-glycosylated IgG heavy chain acid hydrolysis product) can be about 21,600 Da to about 21,700 Da (e.g., 21,673.8 Da). In some cases, the molecular mass of an IgG heavy chain acid hydrolysis product (e.g., a glycosylated IgG heavy chain acid hydrolysis product) can be about 21,750 Da to about 21,850 Da (e.g., 21,803.4 Da). In addition, the methods provided herein can be used to compare the relative abundance of the heavy chain acid hydrolysis products (e.g., IgG heavy chain acid hydrolysis products) as compared to a control or reference sample. As described herein, the IgG heavy chain acid hydrolysis products can include the amino acid sequence set forth in SEQ ID NO:4 (e.g., SEQ ID NO:5, SEQ ID NO:6, or SEQ ID NO:7). In some cases, the abundance of this IgG heavy chain acid hydrolysis product polypeptide sequence can used for diagnosing, treating, and/or monitoring patients with a disease or disorder characterized by altered (e.g., increased) IgG immunoglobulin levels.

In some cases, matrix assisted laser adsorption ionization—TOF (MALDI-TOF) MS can be used to analyze the mass spectrum of a sample. MALDI-TOF MS identifies proteins and peptides as mass charge (m/z) spectral peaks. Further, the inherent resolution of MALDI-TOF MS allows assays to be devised using multiple affinity ligands to selectively purify/concentrate and then analyze multiple proteins in a single assay.

Methods for Assessing IgG Heavy Chain Acid Hydrolysis Products

The materials and methods provided herein can be used for identifying and monitoring heavy chain acid hydrolysis products (e.g., IgG heavy chain acid hydrolysis products). In some cases, the methods provided herein can be used to determine the presence or absence, quantity, and/or glycoform of heavy chain acid hydrolysis products (e.g., IgG heavy chain acid hydrolysis products). For example, the presence or absence, quantity, and/or glycoform of IgG heavy chain acid hydrolysis products can be used for identifying and/or treating a disease or disorder characterized by altered (e.g., increased) IgG immunoglobulin levels in a patient, for monitoring IgG immunoglobulin levels (e.g., therapeutic IgG mAb levels) in a patient, and/or for monitoring treatment of a disease or disorder characterized by altered (e.g., increased) IgG immunoglobulin levels in a patient.

The MS based methods disclosed herein can be used to screen a sample (e.g., a biological sample) for the presence, absence, or amount of immunoglobulins (e.g., IgG immunoglobulins). For example, IgG heavy chain acid hydrolysis products can be used to identify and/or quantify the presence, absence, or amount of IgG immunoglobulins. In some cases, the MS based methods disclosed herein can be used for detecting IgG heavy chain acid hydrolysis products in a sample from a patient.

The MS based methods disclosed herein can include subjecting a sample having one or more immunoglobulins to a MS assay. The sample can be pretreated to isolate or enrich immunoglobulins present in the sample. The immunoglobulin light chains can be decoupled from the immunoglobulin heavy chains prior to the MS analysis. The spectrum obtained from the assay can then be used to identify heavy chain acid hydrolysis products (e.g., IgG heavy chain acid hydrolysis products) in the sample. In some cases, the abundance (e.g., quantity) of IgG heavy chain acid hydrolysis products can be determined by converting the peak areas of one or more of the identified peaks into a molecular mass.

The abundance (e.g., quantity) of the IgG heavy chain acid hydrolysis products can be used to diagnose and/or treat various disorders associated with an altered (e.g., increased or decreased) level of IgG immunoglobulins. In some cases, an altered level of IgG immunoglobulins is an increased (e.g., elevated) level of IgG immunoglobulins. The term "increased level" as used herein with respect to a level of IgG immunoglobulins refers to any level that is greater than the median level of IgG immunoglobulins typically observed in a sample (e.g., a control sample) from one or more healthy (e.g., normal) mammals (e.g., humans). In some cases, the abundance of the IgG immunoglobulins can be compared to a reference value or a control sample. For example, a reference value can be an abundance of IgG immunoglobulins in a healthy patient (e.g., a healthy human). In some cases, a control sample can be a sample (e.g., serum) obtained from one or more healthy patients (e.g., healthy humans). A control sample can be from a single healthy (e.g., normal) mammal, or a control sample can be a pool of samples from two or more (e.g., three, four, five, six, seven, eight, nine, 10, 11, 12, 13, 14, 15, 16, 17, 18, 19, 20, or more) healthy (e.g., normal) mammals.

When diagnosing and/or treating a patient having a disease or disorder characterized by altered (e.g., increased or decreased) immunoglobulin (e.g., IgG immunoglobulin) levels, the disease or disorder can be any appropriate disease or disorder. In some cases, the methods provided herein can be used for treating a patient having increased IgG immunoglobulin levels (also referred to as IgG gammopathies). A gammopathy can be a monoclonal gammopathy, a polyclonal gammopathy, or an oligoclonal gammopathy. Examples of diseases and disorders characterized by increased IgG immunoglobulin levels include, without limitation, multiple myeloma, primary systemic amyloidosis, monoclonal gammopathy of undetermined significance, hepatitis (e.g., autoimmune hepatitis), liver cirrhosis, connective tissue diseases, and infections (e.g., acute, chronic, intrauterine, and perinatal infections). Examples of diseases and disorders characterized by decreased IgG immunoglobulin levels include, without limitation, immune deficiencies (e.g., primary and secondary immune deficiencies), and agammaglobulinemia.

In some cases, the methods provided herein can be used to confirm a diagnosis made by current methods such as gel electrophoresis. For example, if a negative result is obtained from gel electrophoresis, the present methods can be used as a secondary test to confirm or counter such results. In some cases, the diagnosis provided herein can be confirmed using such standard methods.

In some cases, the methods provided herein can be used for treating a patient having altered (e.g., increased or decreased) levels of immunoglobulins (e.g., IgG immunoglobulins). For example, after diagnosing the patient as having a disease or disorder characterized by altered IgG immunoglobulin levels, the methods can include administering to the patient one or more therapeutic agents to treat the disease or disorder characterized by altered IgG immunoglobulin levels (e.g., a therapeutically effective amount) and/or performing a treatment (e.g., a plasma exchange or a stem cell transplant). The therapeutic agent can be any appropriate therapeutic agent. For example, when the disease or disorder is characterized by increased IgG immunoglobulin levels, the therapeutic agent can be any agent useful for reducing IgG immunoglobulin levels. For example, when the disease or disorder is characterized by decreased IgG immunoglobulin levels, the therapeutic agent can increase IgG immunoglobulin levels. Non-limiting examples of agents used to increase IgG immunoglobulin levels include IgG immunoglobulin replacement therapy (e.g., intravenous immunoglobulin (IVIG) replacement therapy and immunoglobulin subcutaneously (IGSC) replacement therapy). In some cases, after diagnosing the patient as having a disease or disorder characterized by altered IgG immunoglobulin levels, the method can include administering to the patient a therapeutically effective amount of a therapeutic agent to treat the disease or disorder characterized by altered IgG immunoglobulin levels and one or more of a plasma exchange and a stem cell transplant (e.g., an autologous peripheral blood stem cell transplantation).

In some cases, the methods provided herein can also be used for monitoring a patient. For example, the MS based methods disclosed herein can be used for monitoring a disease or disorder characterized by altered (e.g., increased or decreased) levels of immunoglobulins (e.g., IgG immunoglobulins) in a patient. The MS based methods disclosed herein can include providing a first sample and a second sample of the patient. For example, the MS based methods disclosed herein can include providing a first sample of the patient before the treatment and a second sample of the patient during or after the treatment. The first and second samples can be pretreated to isolate or enrich immunoglobulins present in the first and second samples. The spectrum obtained from the assay can then be used to identify heavy chain acid hydrolysis products (e.g., IgG heavy chain acid hydrolysis products) in the first and second samples. In some cases, the relative abundance of IgG heavy chain acid hydrolysis products in the first and second samples can be determined by converting the peak areas of one or more of the identified peaks into a molecular mass. The presence or absence of IgG immunoglobulins in the first and second samples can be determined based on the presence or absence of IgG heavy chain acid hydrolysis products in the first and second samples. A decrease (or loss) of the amount of IgG immunoglobulins indicates that the disease or disorder characterized by altered IgG immunoglobulin levels in the patient has been reduced (or eliminated); while an increase in the amount of IgG immunoglobulins indicates that the disease or disorder characterized by altered IgG immunoglobulin levels in the patient has increased. In cases where a first sample of the patient is before the treatment and a second sample of the patient is during or after the treatment, the presence or absence of IgG immunoglobulins is determined before and after the treatment and compared. A decrease (or loss) of the amount of IgG immunoglobulins indicates that the treatment may be effective for the patient; while an increase or no change in the amount of IgG immunoglobulins indicates that the treatment may be ineffective for the patient. For example, the amount of IgG immunoglobulins in a first sample and in a second sample can be determined, and the amount of IgG immunoglobulins in the first sample can be compared to the amount of IgG immunoglobulins and the second sample. For example, the concentration of IgG immunoglobulins in a first sample and in a second sample can be determined, and the concentration of IgG immunoglobulins in the first sample can be compared to the amount of IgG immunoglobulins and the second sample.

The invention will be further described in the following examples, which do not limit the scope of the invention described in the claims.

EXAMPLES

Example 1: Identification of Acid Hydrolysis Products in IgG Purified Serum

Methods

A volume of 50 μL of normal control pooled serum was added to 20 μL of anti-kappa nanobody beads. The serum was allowed to incubate with the nanobody beads for 45 minutes. The beads were washed with 1 mL of PBS 3 times, each time removing and discarding the supernatant. The beads were then washed with water 1 time. The water was removed and 50 μL of 5% acetic acid containing 50 mM TCEP was added to the beads to elute the purified IgG heavy chains with a kappa light chain. This elute was then analyzed by microflow LC-ESI-Q-TOF mass spectrometry using a SCIEX 5600 mass spectrometer.

Results

Figure 1B:
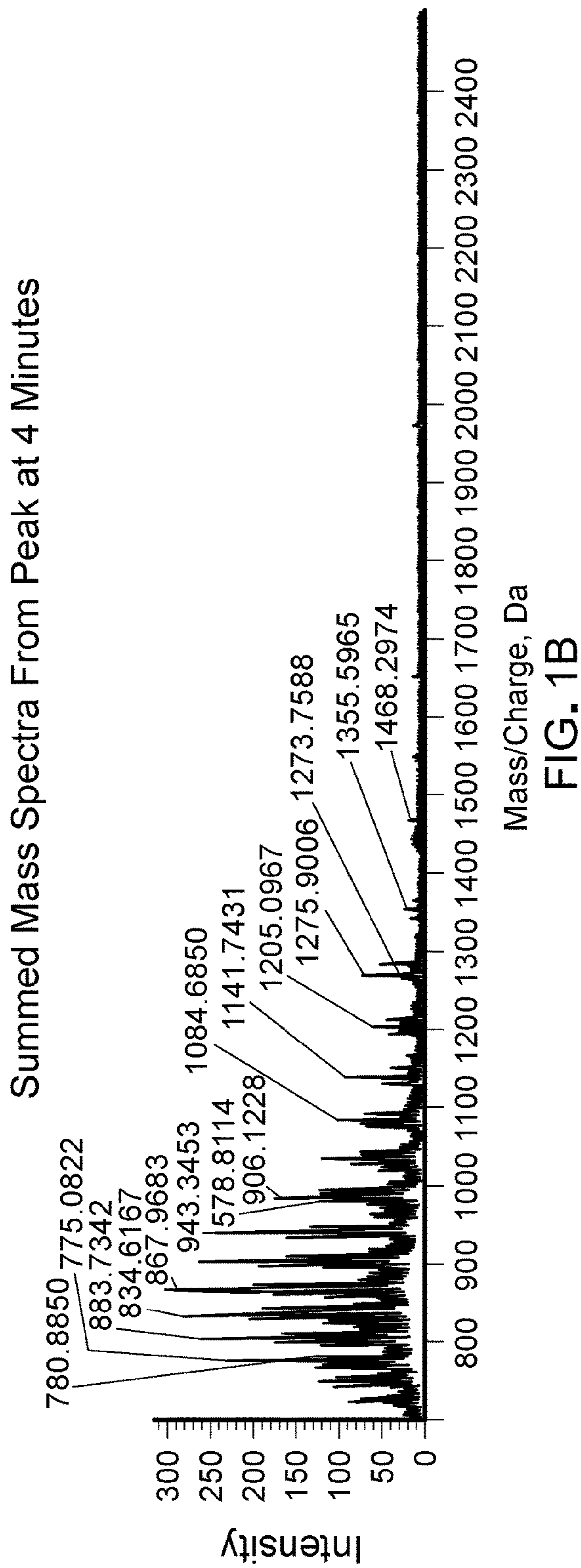
Figure 1C:
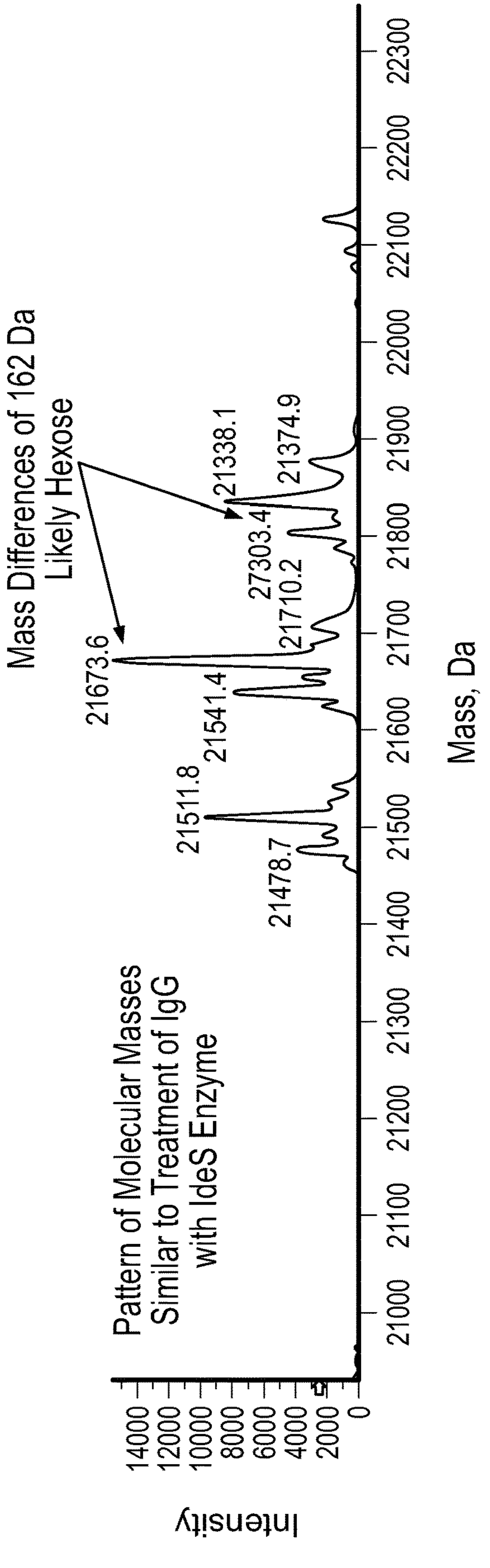

FIG. 1 shows the total ion chromatogram (top) of IgG kappa purified using camelid nanobody beads from normal pooled serum along with the mass spectrum from the unknown peak at 4 minutes (middle). The bottom of the figure shows the deconvoluted mass spectrum which shows the different molecular masses that give a pattern similar to those observed using an enzyme (IdeS) that specifically cleaves IgG heavy chain (FIG. 1). The cause for this unknown peak was not known; however, since the peaks looked similar to those produced by the IdeS enzyme it was suspected that some other process was also cleaving the IgG heavy chain.

Figure 2:
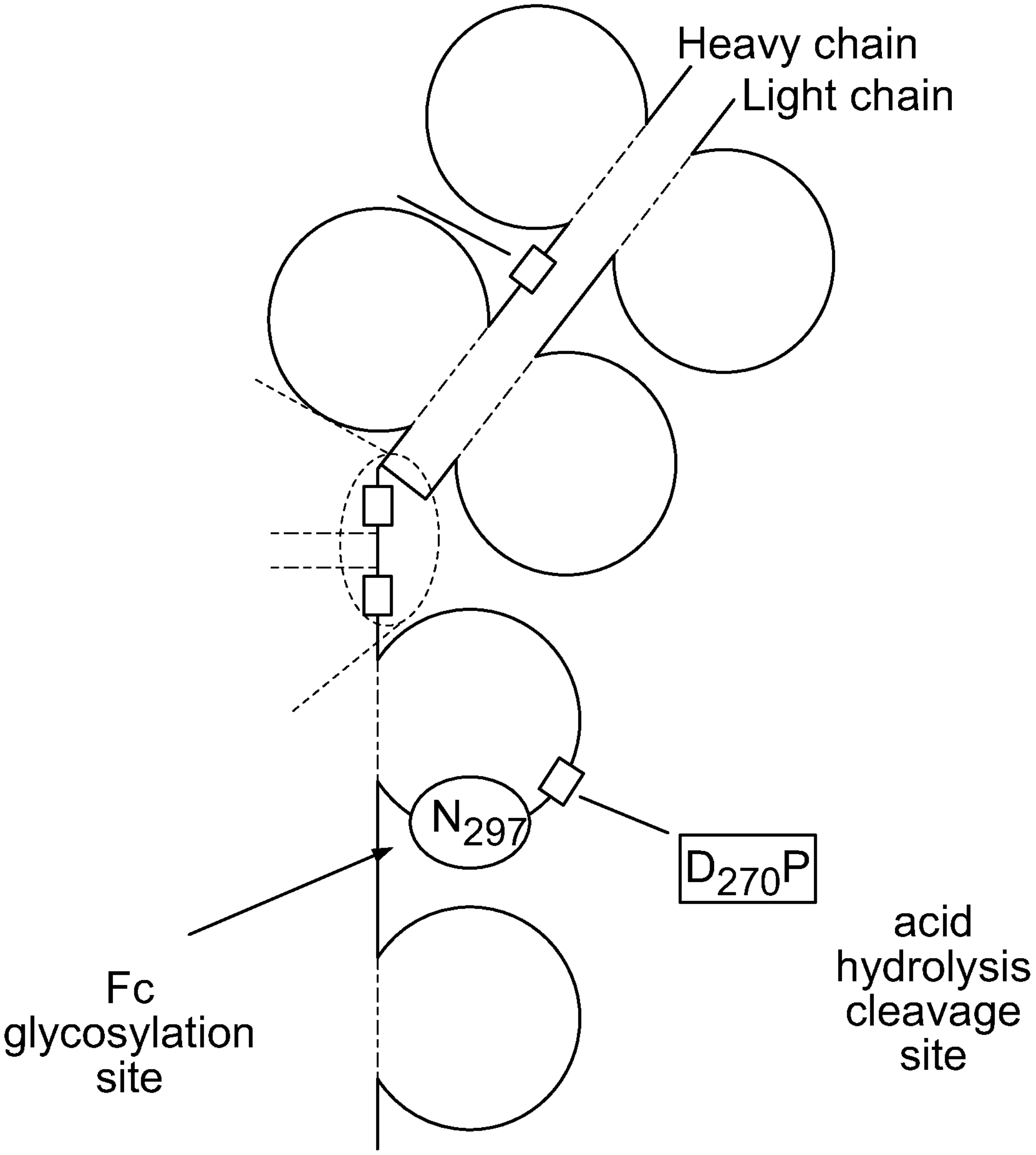
FIG. 2 is a schematic showing some cleavage sites in mAbs. Only one heavy chain and one light chain are shown. Dotted lines represent disulfide bridges. The Fc glycosylation site at asparagine 297 (N297) is also indicated. The acid hydrolysis cleavage site aspartic acid 270 (D270P) is also shown.

Therapeutic IgG monoclonal antibodies (mAbs) were known to be cleaved at aspartic acid 270 (D270; see, e.g., FIG. 2) in IgG heavy chains when exposed to low pH buffer as described elsewhere (see, e.g., Vlasak and Ionescu, 2011, mAbs 3:253-263). To determine if the unknown protein in the bottom of FIG. 1 was an acid hydrolysis cleavage product, the unknown peaks were compared to the peaks generated by IdeS cleavage. The IdeS IgG1 Fc fragment is known (FIG. 3A). Based on the acid hydrolysis cleavage site at D270, a smaller fragment of the IdeS IgG1 Fc fragment should be generated (FIG. 3B) having a theoretical pI/Mw of 4.83/3741.33. The observed unknown fragment at 21,673.8 Da (FIG. 1) and the known IdeS cleavage site matched the number of amino acids lost between the IdeS cleavage site the D270 acid hydrolysis cleavage site, indicating that the unknown protein in the bottom of FIG. 1 was indeed an IgG acid hydrolysis cleavage product.

Figure 4:
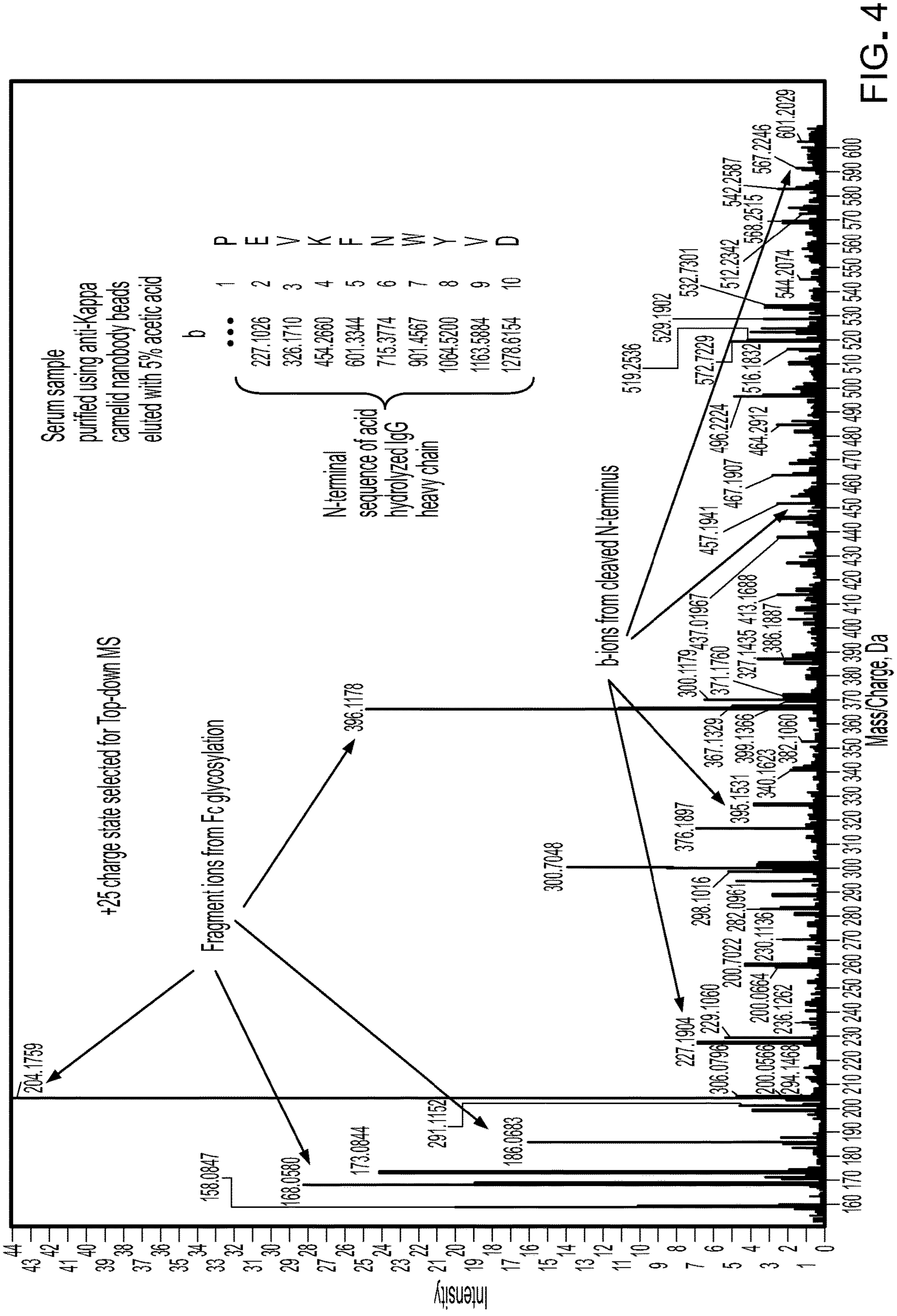
FIG. 4 is a top-down mass spectrum of the +25 charge state from a N-terminal b-ion of an acid hydrolyzed IgG heavy chain (SEQ ID NO:5) resulting from cleavage at D270.

The sequence of the IgG heavy chain acid hydrolysis products in FIG. 1 were confirmed as PEVKFNWYVD (SEQ ID NO:5) using top-down MS (FIG. 4). The b-ions observed confirm that acid hydrolysis of IgG heavy chains with 5% acetic acid generated the IgG heavy chain acid hydrolysis products observed in the serum sample. These results demonstrate that IgG heavy chain acid hydrolysis cleavage products can be identified using MS techniques without the Ides enzyme.

Mass spectra were obtained for the serum samples cleaved using IdeS enzyme and hydrolyzed using 5% acetic acid. The molecular mass of the IgG heavy chain cleavage fragments (including the mass differences in the glycoforms) produced by cleavage with the IdeS enzyme match those obtained by acid hydrolysis (compare FIGS. 5A and 5B). These results demonstrate that different glycoforms of IgG heavy chain acid hydrolysis cleavage products can be identified using MS techniques without the Ides enzyme.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a subclass of an IgG in a biological sample, the method comprising:
   - providing a biological sample comprising immunoglobulins;
   - immunopurifying IgG immunoglobulins from the biological sample to generate a polyclonal IgG-purified sample;
   - subjecting the polyclonal IgG-purified sample to an acid to hydrolyze the IgG immunoglobulins and generate IgG acid hydrolysis products comprising IgG heavy chain acid hydrolysis products;
   - analyzing the IgG acid hydrolysis products by a mass spectrometry technique to obtain a mass spectrum of the IgG acid hydrolysis products; and
   - identifying the IgG acid heavy chain acid hydrolysis products based on the multiply charged ion peaks in the spectrum, wherein the ion peaks of the of IgG heavy chain acid hydrolysis products are in the range of 21,600 to 21,700 Da when the IgG heavy chains are not glycosylated and are in the range of 21,750 to 21,850 Da when the IgG heavy chains are glycosylated; and
   - identifying the subclass of the IgG based on a sequence corresponding to the multiply charged ion peaks of the heavy chain acid hydrolysis products, wherein the IgG is determined to be: a) IgG1 when the sequence at the N-terminus of the heavy chain acid hydrolysis products is PEVKFNWYVD (SEQ ID NO:5), b) IgG2 or IgG4 when the sequence at the N-terminus of the heavy chain acid hydrolysis products is PEVQFNWYVD (SEQ ID NO:6), or c) IgG3 when the sequence at the N-terminus of the heavy chain acid hydrolysis products is PEVQFKWYVD (SEQ ID NO:7).

2. The method of claim 1, wherein said acid is acetic acid.

3. The method of claim 2, wherein said acetic acid is 5% acetic acid.

4. The method of claim 1, wherein said biological sample is a biological fluid selected from the group consisting of blood, serum, plasma, urine, lachrymal fluid, and saliva.

5. The method of claim 1, wherein said immunopurifying comprises using an anti-human IgG kappa antibody.

6. The method of claim 5, wherein said anti-human IgG kappa antibody is a non-human antibody selected from the group consisting of a camelid antibody, a cartilaginous fish antibody, a llama antibody, a sheep antibody, a goat antibody, a rabbit antibody, and a mouse antibody.

7. The method of claim 5, wherein said anti-human IgG kappa antibody is a single domain antibody fragment.

8. The method of claim 1, wherein said mass spectrometry technique comprises a liquid chromatography-mass spectrometry (LC-MS) technique.

9. The method of claim 1, wherein the mass spectrometry technique is electrospray ionization mass spectrometry (ESI-MS), and wherein the ESI-MS technique comprises a quadrupole time-of-flight (TOF) mass spectrometer.

10. The method of claim 1, wherein the mass spectrometry technique is a top-down mass spectrometry technique.

11. The method of claim 1, wherein said immunoglobulins are not fragmented during the mass spectrometry technique.

12. The method of claim 1, said method further comprising contacting the IgG acid hydrolysis products with a reducing agent prior to subjecting the IgG acid hydrolysis products to the mass spectrometry technique.

13. The method of claim 12, wherein the reducing agent is tris(2-carboxyethyl) phosphine (TCEP).

14. The method of claim 1, wherein said immunopurifying comprises using an anti-human IgG lambda antibody.

15. The method of claim 14, wherein said anti-human IgG lambda antibody is a non-human antibody selected from the group consisting of a camelid antibody, a cartilaginous fish antibody, a llama antibody, a sheep antibody, a goat antibody, a rabbit antibody, and a mouse antibody.

16. The method of claim 14, wherein said anti-human IgG lambda antibody is a single domain antibody fragment.

* * * * *